United States Patent
Uno et al.

(10) Patent No.: US 12,281,092 B2
(45) Date of Patent: Apr. 22, 2025

(54) COMPOUND OR SALT THEREOF, COMPOSITION, CHEMILUMINESCENCE METHOD, METHOD FOR MEASURING CHEMILUMINESCENCE SIGNAL, REAGENT, REAGENT KIT, AND METHOD FOR ASSAYING ANALYTE

(71) Applicant: SYSMEX CORPORATION, Kobe (JP)

(72) Inventors: Shinnosuke Uno, Kobe (JP); Takuya Kubo, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 19 days.

(21) Appl. No.: 18/158,006

(22) Filed: Jan. 23, 2023

(65) Prior Publication Data
US 2023/0242499 A1     Aug. 3, 2023

(30) Foreign Application Priority Data
Jan. 28, 2022   (JP) ................. 2022-012252

(51) Int. Cl.
| | | |
|---|---|---|
| C07D 315/00 | (2006.01) | |
| C07D 407/12 | (2006.01) | |
| C07F 5/02 | (2006.01) | |
| C07F 9/09 | (2006.01) | |

(52) U.S. Cl.
CPC ......... *C07D 315/00* (2013.01); *C07D 407/12* (2013.01); *C07F 5/027* (2013.01); *C07F 9/091* (2013.01)

(58) Field of Classification Search
CPC ............................ C07D 315/00; C07D 407/12
See application file for complete search history.

(56) References Cited

U.S. PATENT DOCUMENTS

| | | |
|---|---|---|
| 5,236,849 A | 8/1993 | Ishikawa |
| 10,660,974 B2 | 5/2020 | Shabat et al. |
| 2019/0290787 A1 | 9/2019 | Shabat et al. |

FOREIGN PATENT DOCUMENTS

| | | | |
|---|---|---|---|
| CN | 111378153 A | * | 7/2020 |
| EP | 3408349 B1 | | 3/2021 |
| JP | 2837276 B2 | | 12/1998 |
| JP | 5092254 B2 | | 12/2012 |
| JP | 2019-509981 A | | 4/2019 |
| JP | 6916943 B2 | | 8/2021 |
| WO | 2017/130191 A1 | | 8/2017 |
| WO | 2021/086977 A1 | | 5/2021 |

OTHER PUBLICATIONS

Matsumoto et al. Heterocycles 1995, 41, 2419-2422 (Year: 1995).*
Ertl, P. Chemistry—Methods, 2002, 2, e202200041 (Year: 2002).*
Matsumoto et al. Tetrahedron Letters 2004, 45, 8079-8082 (Year: 2004).*
CAS Registry Entry for Registry No. 173438-85-2, which entered STN on Feb. 23, 1996 (Year: 1996).*
CAS Registry Entry for Registry No. 173438-86-3, which entered STN on Feb. 23, 1996 (Year: 1996).*
CAS Registry Entry for Registry No. 796875-52-0, which entered STN on Dec. 13, 2004 (Year: 2004).*
Corwin Hansch et al: "A Survey of Hammett Substituent Constants and Resonance and Field Parameters". Chemical Reviews, 1991, vol. 91, No. 2, pp. 165-195, American Chemical Society; Cited in the Specification.
Biosynth Carbosynth: "Product Minireviews: Exploring New Territories With Dioxetanes Chemiluminescence", 2018, 14 pages in total.
Nir Hananya et al: "Rapid chemiexcitation of phenoxy-dioxetane luminophores yields ultrasensitive chemiluminescence assays", Chemical Science, 2019, vol. 10, No. 5, pp. 1380-1385, The Royal Society of Chemistry.
Ori Green et al: "Opening a Gateway for Chemiluminescence Cell Imaging: Distinctive Methodology for Design of Bright Chemiluminescent Dioxetane Probes", ACS Central Science, 2017, vol. 3, No. 4, pp. 349-358, American Chemical Society.
James Ashenhurst: "Exploring Resonance: Pi-acceptors", Master Organic Chemistry, LLC, Last updated: Dec. 28, 2022, Webpage URL: https://www.masterorganicchemistry.com/2011/12/19/exploring-resonance-pi-acceptors/.
Pubchem, "5'-[[3-Hydroxy-5-(2,6,7-trioxa-4,4-dimethyl-5-tert-butylbicyclo[3.2.0]heptane-1-yl)phenyl]ethynyl]-3,6-dihydroxyspiro[9H-xanthene-9,1'(3'H)-isobenzofuran]-3'-one", Retrieved from the Internet: URL:https://pubchem.ncbi.nlm.nih.gov/compound/102327135, 2015, 7 pages in total.
Masakatsu Matsumoto et al., "Synthesis and Chemiluminescence of 3-Biphenylyl-4,4-Diisopropyl-3-Methoxy-1,2-Dioxetanes", Heterocycles, 1995, pp. 2419-2422, vol. 41, No. 11.
Masakatsu Matsumoto et al., "Color modulation for intramolecular charge-transfer-induced chemiluminescence of bicyclic dioxetanes bearing a 3-hydroxy-5-naphthylphenyl moiety in the coordination sphere", Tetrahedron Letters, 2006, pp. 8407-8411, vol. 47, Elsevier Ltd.
Masakatsu Matsumoto et al., "Color modulation for chemiluminescence of a dioxetane bearing a 3-(anthracen-9-yl)-5-hydroxyphenyl moiety induced by a complex of crown ether with potassium tert-butoxide", Tetrahedron Letters, 2004, pp. 8079-8082, vol. 45, Elsevier Ltd.
Nobuko Watanabe et al., "Highly effective and rapid emission of light from bicyclic dioxetanes bearing a 3-hydroxyphenyl substituted with a 4-p-oligophenylene moiety in an aqueous system: Two different ways for the enhancement of chemiluminescence efficiency", Tetrahedron, 2020, Article No. 131203 (11 pages in total), vol. 76, Elsevier Ltd.

(Continued)

Primary Examiner — Matthew P Coughlin
(74) Attorney, Agent, or Firm — Sughrue Mion, PLLC

(57) ABSTRACT

Disclosed is a compound represented by formula [I] according to the specification, or a salt thereof, a composition comprising the compound, a chemiluminescence method using the compound, a method for measuring chemiluminescence signal, a reagent comprising the compound, a reagent kit comprising the compound and a method for assaying analyte.

14 Claims, 6 Drawing Sheets

(56) References Cited

OTHER PUBLICATIONS

Ilke Simsek Turan et al., "A sensitive and selective chemiluminogenic probe for palladium", RSC Advances, 2015, pp. 34535-34540, vol. 5, The Royal Society of Chemistry.
Yuqi Gao et al., "A specific and selective chemiluminescent probe for Pd2+ detection", Chinese Chemical Letters, 2019, pp. 63-66, vol. 30, Elsevier B.V.
Extended European search report issued on May 26, 2023 in a counterpart European patent application No. 23153578.2.

* cited by examiner

COMPOUND OR SALT THEREOF, COMPOSITION, CHEMILUMINESCENCE METHOD, METHOD FOR MEASURING CHEMILUMINESCENCE SIGNAL, REAGENT, REAGENT KIT, AND METHOD FOR ASSAYING ANALYTE

CROSS REFERENCE TO RELATED APPLICATIONS

This application claims priority from prior Japanese Patent Application No. 2022-012252, filed on Jan. 28, 2022, entitled "COMPOUND OR SALT THEREOF, COMPOSITION, CHEMILUMINESCENCE METHOD, METHOD FOR MEASURING CHEMILUMINESCENCE SIGNAL, REAGENT, REAGENT KIT, AND METHOD FOR ASSAYING ANALYTE", the entire contents of which are incorporated herein by reference.

FIELD OF THE INVENTION

The present disclosure relates to a compound or a salt thereof, a composition, a chemiluminescence method, a method for measuring chemiluminescence signal, a reagent, a reagent kit and a method for assaying an analyte.

BACKGROUND 1,2-Dioxetane derivative is a compound capable of inducing chemiluminescence, triggered by a reaction with a chemical substance such as enzyme. For example, U.S. Patent No. 2019/290787 discloses a compound represented by formula IVb:

[Chemical Formula 1]

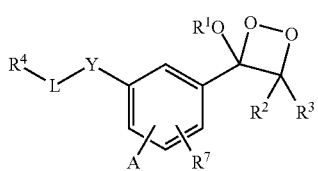

IVb wherein A represents a π* acceptor group such as —CN, —CH═CH-E, with the π* acceptor group bound to an ortho position or a para position of -Y-L-R⁴ group.

SUMMARY OF THE INVENTION

The scope of the present invention is defined solely by the appended claims, and is not affected to any degree by the statements within this summary.

An object of the present disclosure is to provide a compound or a salt thereof that exhibits high luminous efficiency, as well as a composition, a reagent, and a reagent kit that contain the compound or the salt thereof. Another object of the present disclosure is to provide a chemiluminescence method, a method for measuring a chemiluminescence signal, and a method for assaying an analyte, all with use of such compound or the salt thereof.

Aiming at solving the problem, the present inventors found from our thorough investigations that high luminous efficiency is demonstrated by a compound in which a benzene ring, bound to the 3-position of 1,2-dioxetane, has a specific substituent, that is, —C≡C-E (wherein E represents —COOH, —H, —CN, —COO-alkyl, or, an aryl group, a pyridinyl group, a pyridinium group, a 3H-indolyl group, or a 3H-indol-1-ium group, optionally substituted with a substituent), or an aryl group substituted with an electron withdrawing group.

The present disclosure encompasses the following embodiments.

[Item 1]

A compound represented by formula [I], or a salt thereof:

[Chemical Formula 2]

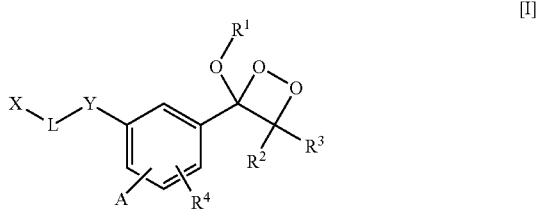

[I]

[wherein,

R¹ represents a $C_{1-8}$ alkyl group, each of R² and R³ independently represents a $C_{3-18}$ alkyl group or a $C_{3-7}$ cycloalkyl group;

R¹ and R², R¹ and R³, or R² and R³, together with a carbon atom to which they are bound, may form an optionally substituted ring;

X represents H or a caging group;

L is absent or represents a linker represented by formula L1, L2, L3, or L4:

[Chemical Formula 3]

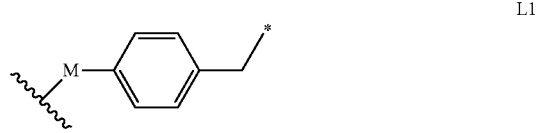

L1

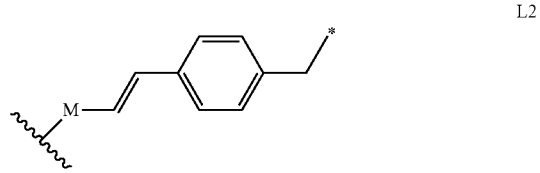

L2

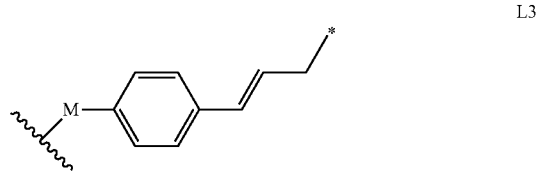

L3

L4

(in each formula,

M is absent or represents —O— or —NH—, a wavy line represents a linkage point to X, an asterisk represents a linkage point to Y);

a benzene ring in Formulae L1, L2, and L3 may be substituted with a substituent selected from the group consisting of halo group, alkyl group, cycloalkyl group, and alkoxy group;

Y is absent or represents —O— or —NH—;

R⁴ represents H or an electron withdrawing group bound to an ortho or a para position of the -Y-L-X group;

A represents —C≡C-E (where, E represents —COOH, —H, —CN, —COO-alkyl, or, an aryl group, a pyridinyl group, a pyridinium group, a 3H-indolyl group, or a 3H-indol-1-ium group, optionally substituted with a substituent), or an aryl group substituted with an electron withdrawing group].

[Item 2]
The compound or the salt thereof according to item 1, wherein A is bound to the ortho position or the para position of the -Y-L-X group.

[Item 3]
The compound or the salt thereof according to item 1 or 2, wherein A represents —C≡C-E bound to the ortho position of the -Y-L-X group.

[Item 4]
The compound or the salt thereof according to any one of items 1 to 3, wherein E represents —COOH, —H, —CN, —COO—$C_{1-8}$ alkyl, phenyl, —$C_6H_4O$—$C_{1-8}$ alkyl, —$C_6H_4COOH$, —$C_6H_4COO$—$C_{1-8}$ alkyl, 4-pyridinyl, methylpyridinium-4-yl, 3,3-dimethyl-3H-indolyl, or 1,3,3-trimethyl-3H-indol-1-ium-2-yl.

[Item 5]
The compound or the salt thereof according to item 1 or 2, wherein A represents an aryl group bound to the ortho position of the -Y-L-X group,
the aryl group is substituted with an electron withdrawing group selected from the group consisting of —$COOR^8$, halo group, —OH, —$NO_2$, —CN, —CO—$R^9$, and —$SO_2$-$R^{10}$,
and each of $R^8$, $R^9$, and $R^{10}$ independently represents H or a $C_{1-18}$ alkyl group.

[Item 6]
The compound or the salt thereof according to item 1 or 2, wherein A represents a phenyl group bound to the ortho position of the -Y-L-X group,
the phenyl group is substituted with an electron withdrawing group selected from the group consisting of —$COOR^8$, halo group, —OH, —$NO_2$, —CN, —CO—$R^9$, and —$SO_2$-$R^{10}$, and each of $R^8$, $R^9$, and $R^{10}$ independently represents H or a $C_{1-8}$ alkyl group.

[Item 7]
The compound or the salt thereof according to any one of items 1 to 6, wherein $R^4$ represents H, or a halo group or —CN bound to the ortho position or the para position of the -Y-L-X group.

[Item 8]
The compound or the salt thereof according to any one of items 1 to 7, wherein $R^4$ represents H, or a halo group or —CN bound to the ortho position of the -Y-L-X group.

[Item 9]
The compound or the salt thereof according to any one of items 1 to 8, wherein X represents H, trialkylsilyl group, (2,4-dinitrophenyl)sulfonyl group, 3,4,6-trimethyl-2,5-dioxobenzyl group, 2-(3-carboxy-4-nitrophenyl)-S—S-ethyloxycarbonyl group, 4-azidobenzyloxycarbonyl group, or a group represented by formula X1, X2, X3, X4, X5, X6, or X7:

[Chemical Formula 4]

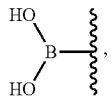
X1

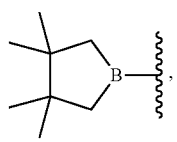
X2

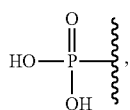
X3

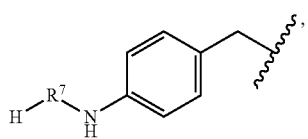
X4

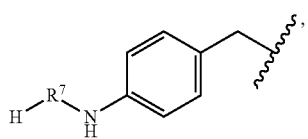

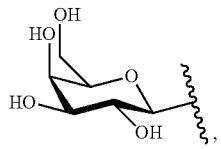
X5

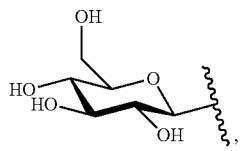
X6

X7

(wherein,
$R^7$ represents one amino acid residue, or a group formed of a sequence of a plurality of amino acid residues, with a C-terminal of the group bound to NH, and the wavy line represents a linkage point to L).

[Item 10]
The compound or the salt thereof according to any one of items 1 to 9, satisfying any one of (1) to (4) below:
(1) Y represents —O— or —NH—, L is absent, and X represents H;
(2) Y represents —O— or —NH—, L is absent, and X represents a group represented by formula X3:

[Chemical Formula 5]

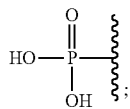
X3

(3) Y represents —O— or —NH—, L represents a linker represented by formula L1, L2, L3 or L4, M represents —O— or —NH—, and X represents a caging group; or (4) Y is absent, L is absent, and X represents a group represented by formula X1 or X2:

[Chemical Formula 6]

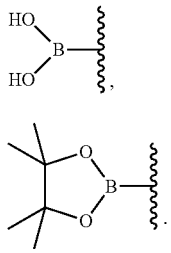

[Item 11]
The compound or the salt thereof according to any of items 1 to 10, wherein $R^2$ and $R^3$, together with the carbon atom to which they are bound, form an optionally substituted condensed ring, a spiro ring, or a bridged ring.

[Item 12]
The compound or the salt thereof according to any of items 1 to 11, wherein $R^2$ and $R^3$, together with the carbon atom to which they are bound, form an adamantane ring optionally substituted with a halo group.

[Item 13]
A composition containing the compound or the salt thereof according to any one of items 1 to 12, and an aqueous solvent.

[Item 14]
The composition according to item 13, wherein X represents a caging group.

[Item 15]
The composition according to item 13 or 14, further containing a surfactant.

[Item 16]
A chemiluminescence method including reacting the compound or the salt thereof whose X representing a caging group according to any one of items 1 to 12, with a substance that releases the caging group.

[Item 17]
The chemiluminescence method according to item 16, wherein X represents a caging group represented by formula X3:

[Chemical Formula 7]

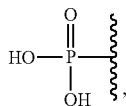

and
the substance that releases the caging group is alkaline phosphatase.

[Item 18]
A method for measuring a chemiluminescence signal, the method comprising measuring a chemiluminescence signal generated by the chemiluminescence method according to item 16 or 17.

[Item 19]
A reagent for assaying an analyte in a sample, the reagent comprising the compound or the salt thereof according to any one of items 1 to 12.

[Item 20]
A reagent kit for assaying an analyte in a sample, the reagent kit comprising:
a first reagent comprising: the compound or the salt thereof according to any one of items 1 to 12, wherein X represents a caging group; and
a second reagent comprising a substance that releases the casing group.

[Item 21]
A method for assaying an analyte in a sample, the method comprising:
forming, on a solid phase, an immune complex that comprises: the analyte; a capture body that binds to the analyte; and a detector that comprises a substance that binds to the analyte and releases a caging group;
reacting the substance that releases the caging group in the immune complex, with the compound or the salt thereof according to any one of items 1 to 12, wherein X represents a caging group, to generate a chemiluminescence signal; and
assaying the chemiluminescence signal to assay the analyte.

The present disclosure successfully provides a compound or a salt thereof that exhibits high luminous efficiency, as well as a composition, a reagent, and a reagent kit that contain the compound or the salt thereof. The present disclosure also successfully provides a chemiluminescence method, a method for measuring a chemiluminescence signal, and a method for assaying an analyte, all with use of such compound or the salt thereof.

DETAILED DESCRIPTION OF THE PREFERRED EMBODIMENTS

1. Definition

Figure 1A:
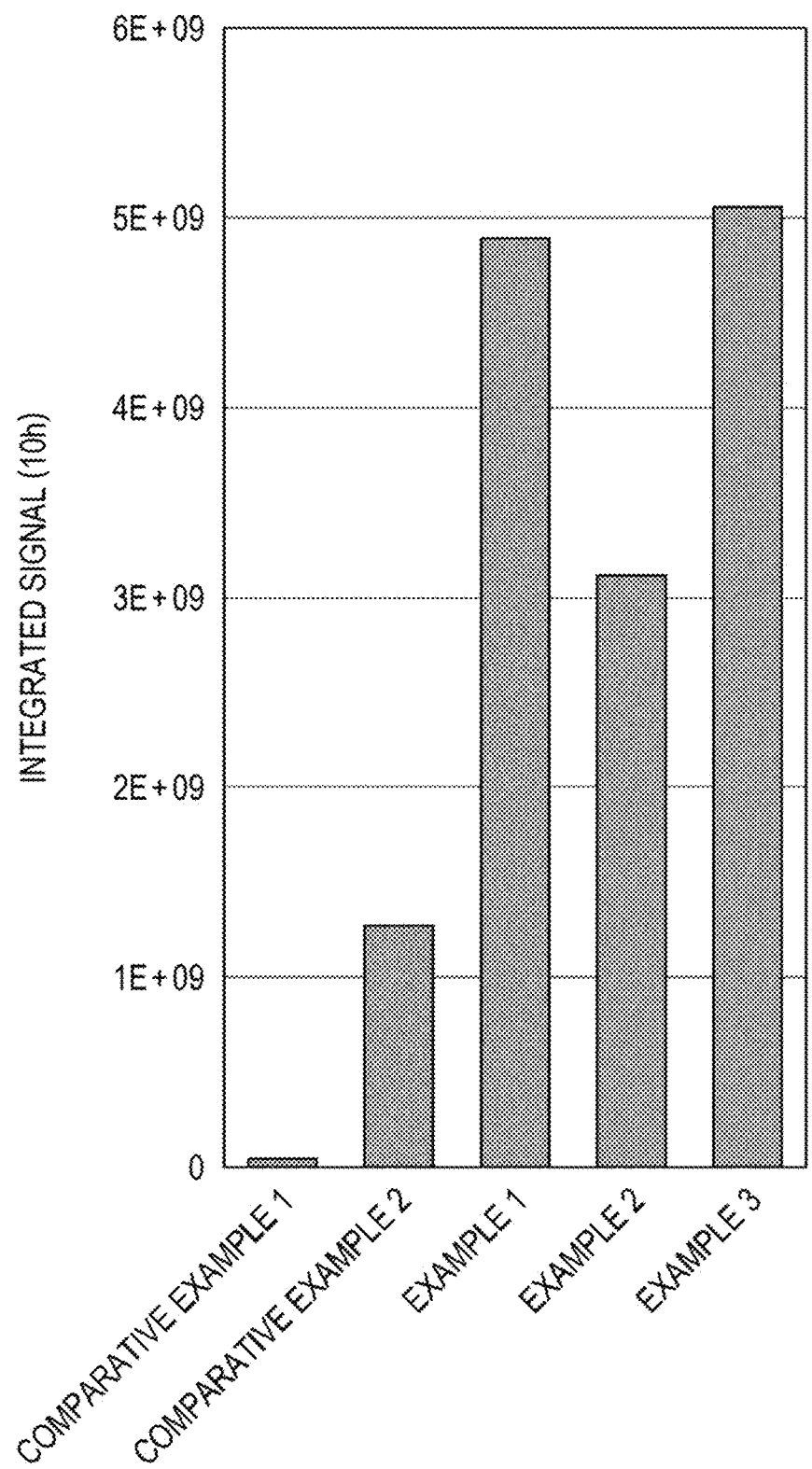
FIG. 1A is a graph comparing luminous efficiency of Examples 1 to 3, with luminous efficiency of Comparative Examples 1 and 2.

In the present specification, the halo group refers to a monovalent group composed of halogen. The halo group is exemplified by fluoro group (—F), chloro group (—Cl), bromo group (—Br), and iodo group (—I).

In the present specification, the alkyl group refers to a monovalent group obtained by removing one hydrogen atom from a linear or branched saturated hydrocarbon. The number of carbon atoms in the alkyl group is typically 1 to 20, although not particularly limited. The alkyl group is exemplified by methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, n-heptyl group, isoheptyl group, n-octyl group, isooctyl group, 2-ethylhexyl group, n-nonyl group, isononyl group, n-decyl group, isodecyl group, n-undecyl group, n-dodecyl group (lauryl group), isolauryl group, n-tridecyl group, isotridecyl group, n-tetradecyl group (myristyl group), isomyristyl group, n-pentadecyl group, isopentadecyl group, n-hexadecyl group (palmityl group), isopalmityl group, n-heptadecyl group, isoheptadecyl group, n-octadecyl group (stearyl group), and isostearyl group.

In the present specification, the $C_{1-8}$ alkyl group refers to a linear or branched alkyl group having 1 to 8 carbon atoms. The $C_{1-8}$ alkyl group is exemplified by methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, n-heptyl group, isoheptyl group, n-octyl group, isooctyl group, and 2-ethylhexyl group.

In the present specification, the $C_{3-18}$ alkyl group refers to a linear or branched alkyl group having 3 to 18 carbon atoms. The $C_{3-18}$ alkyl group is exemplified by n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, n-heptyl group, isoheptyl group, n-octyl group, isooctyl group, 2-ethylhexyl group, n-nonyl group, isononyl group, n-decyl group, isodecyl group, n-undecyl group, n-dodecyl group (lauryl group), isolauryl group, n-tridecyl group, isotridecyl group, n-tetradecyl group (myristyl group), isomyristyl group, n-pentadecyl group, isopentadecyl group, n-hexadecyl group (palmityl group), isopalmityl group, n-heptadecyl group, isoheptadecyl group, n-octadecyl group (stearyl group), and isostearyl group.

In the present specification, the cycloalkyl group refers to a monovalent group derived from saturated aliphatic hydrocarbon ring. The number of carbon atoms in the cycloalkyl group is typically 3 to 20, although not particularly limited. The cycloalkyl group is exemplified by cyclopropyl group, cyclobutyl group, cyclopentyl group, cyclohexyl group, cycloheptyl group, cyclooctyl group, cyclononyl group, cyclodecyl group, norbornyl group, and adamantyl group.

In the present specification, the $C_{3-7}$ cycloalkyl group refers to a cycloalkyl group having 3 to 7 carbon atoms. The $C_{3-7}$ cycloalkyl group is specifically exemplified by cyclopropyl group, cyclobutyl group, cyclopentyl group, cyclohexyl group, and cycloheptyl group.

In the present specification, the aryl group refers to a monovalent group derived from aromatic hydrocarbon ring. The number of carbon atoms in the aryl group is typically 6 to 20, although not particularly limited. The aryl group is exemplified by phenyl group, indenyl group, naphthyl group, fluorenyl group, phenanthrenyl group, and anthracenyl group.

In the present specification, the alkoxy group refers to a group represented by —O-alkyl. The alkyl in this group is synonymous to the aforementioned "alkyl group". The alkoxy group is exemplified by methoxy group, ethoxy group, n-propoxy group, isopropoxy group, n-butoxy group, isobutoxy group, sec-butoxy group, tert-butoxy group, n-pentoxy group, isopentoxy group, neopentoxy group, tert-pentoxy group, n-hexoxy group, and isohexoxy group.

In the present specification, the caging group (also referred to as protecting group) refers to a group that prevents generation of unstable chemical species such as 1,2-dioxetanylphenolate. The caging group may be uncaged (or deprotected) by chemical processes such as hydrogenolysis, hydrolysis, and enzymatic reaction, or by physical processes such as electrolysis and photolysis. The chemical species generated by uncaging may typically be brought up to an excited state, and may emit light when falling from the excited state down to the ground state.

The caging group is exemplified by trialkylsilyl group, dialkylmonoarylsilyl group, monoalkyldiarylsilyl group, and triarylsilyl group. The trialkylsilyl group is exemplified by tri($C_{1-4}$ alkyl)silyl group such as trimethylsilyl group, triethylsilyl group, triisopropylsilyl group, and tert-butyldimethylsilyl group. The dialkylmonoarylsilyl group is exemplified by di($C_{1-4}$ alkyl)mono($C_{6-10}$ aryl)silyl group such as a dimethylphenylsilyl group. The monoalkyldiarylsilyl group is exemplified by mono($C_{1-4}$ alkyl)di($C_{6-10}$ aryl)silyl group such as a tert-butyldiphenylsilyl group. The triarylsilyl group is exemplified by tri($C_{6-10}$ aryl)silyl group such as a triphenylsilyl group.

Other examples of the caging group include (2,4-dinitrophenyl)sulfonyl group, 3,4,6-trimethyl-2,5-dioxobenzyl group, 2-(3-carboxy-4-nitrophenyl)-S—S-ethyloxycarbonyl group, and 4-azidobenzyloxycarbonyl group.

Yet another example of the caging group includes a group represented by formula X1, X2, X3, X4, X5, X6, or X7:

[Chemical Formula 8]

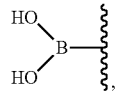

X1

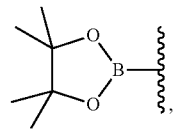

X2

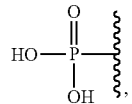

X3

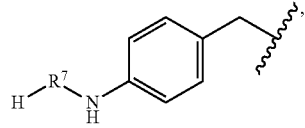

X4

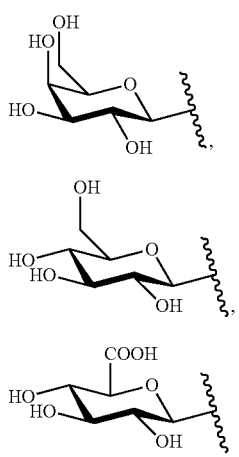

(wherein:

R[7] represents one amino acid residue, or a group formed of a sequence of a plurality of amino acid residues, with the C-terminal of these groups bound to NH, and the wavy line represents a linkage point to L).

In the present specification, the substance that functions to release (or remove) the caging group may occasionally be referred to as an uncaging substance. The uncaging substance may be glutathione if X represents (2,4-dinitrophenyl)sulfonyl group;

may be hydrogen peroxide for X representing a group represented by formula X2;

may be alkaline phosphatase for X representing a group represented by formula X3;

may be enzyme for X representing a group represented by formula X4, whose R[7] having an amino acid sequence (for example, cathepsin B-cleavable amino acid sequence such as those containing Phe-Lys, citrullin-Val, or Gly-Phe-Leu-Gly; legumain-cleavable amino acid sequence such as those containing N-carbobenzoyl-Ala-Ala-Asn-ethylenediamine; γ-glutamyl transpeptidase-cleavable amino acid sequence such as those containing γ-Glu-); and may be β-galactosidase for X representing a group represented by formula X5 (β-galactosyl group).

In the present specification, the amino acid residue is typically referred to as a group represented by the following formula:

[Chemical Formula 9]

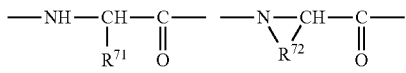

(wherein, each of R[71] and R[72] independently represents a side chain composed of an amino acid). The amino acid residue is exemplified by glycine residue, alanine residue, valine residue, leucine residue, isoleucine residue, serine residue, threonine residue, cysteine residue, methionine residue, aspartic acid residue, glutamic acid residue, lysine residue, arginine residue, asparagine residue, glutamine residue, phenylalanine residue, tyrosine residue, histidine residue, tryptophan residue, and proline residue.

In the present specification, the electron withdrawing group refers to a functional group having a positive value for Hammett substituent constant σp. The definition of σp, and σp values of the individual functional groups may be understood typically referring to Hansch, C et al., Chem. Rev., 91, pp. 165-195 (1991). The "electron withdrawing group" is exemplified by halo group, —OH, —NO$_2$, —CN, —COOH, —COO—C$_{1-18}$ alkyl, —COH, —CO—C$_{1-18}$ alkyl, —SO$_2$H, and -SO$_2$-C$_{1-18}$ alkyl.

In the present specification, the sample is a material to be tested collected from living body, which means a material that possibly contains an analyte. The sample may be either a liquid material or a solid material. The liquid material is exemplified by blood material, cerebrospinal fluid, sputum, bronchoalveolar lavage fluid, nasopharyngeal swab, lymph fluid, urine, feces, and saliva. The blood material includes plasma, serum, and whole blood. The liquid material may be a solubilized matter of a solid material. The solid material is exemplified by excised tissue. Detection of the analyte includes in vitro detection of the analyte in the sample, and in vivo detection of the analyte in the sample.

In the present specification, the analyte means a substance in the sample, detectable by a later-described chemiluminescence probe, the composition, the reagent, the reagent kit, or the method for assaying the analyte. The analyte is exemplified by protein, peptide, and nucleic acid. These analytes may exist in a free state in the sample, or may exist typically on the surface or inside of cell, lipoprotein, vesicle, and virus.

2. Compound Represented by Formula [I], or Salt Thereof

The present inventors have found that high luminous efficiency is demonstrated by the compound in which A represents —C≡C-E (wherein E represents —COOH, —H, —CN, —COO-alkyl, or, an aryl group, a pyridinyl group, a pyridinium group, a 3H-indolyl group, or a 3H-indol-1-ium group, optionally substituted with a substituent), or an aryl group substituted with an electron withdrawing group.

A is preferably bound to the ortho position or the para position of the -Y-L-X group, and more preferably bound to the ortho position of the -Y-L-X group.

In one embodiment, A is preferably —C≡C-E bound to the ortho position or the para position of the -Y-L-X group, and more preferably —C≡C-E bound to the ortho position of the -Y-L-X group.

With E representing an aryl group, a pyridinyl group, a pyridinium group, a 3H-indolyl group, or a 3H-indol-1-ium group, optionally substituted with a substituent, the number of the substituent may be one or more (for example, two, three, or four).

E is preferably —COOH, —H, —CN, —COO—C$_{1-8}$ alkyl, phenyl, —C$_6$H$_4$O—C$_{1-8}$ alkyl, —C$_6$H$_4$COOH, —C$_6$H$_4$COO—C$_{1-8}$ alkyl, 4-pyridinyl, methylpyridinium-4-yl, 3,3-dimethyl-3H-indolyl, or 1,3,3-trimethyl-3H-indol-1-ium-2-yl; more preferably —COOH, —H, —CN, —COO—C$_{1-4}$ alkyl, —C$_6$H$_4$COOH, or —C$_6$H$_4$COO—C$_{1-4}$ alkyl; and even more preferably —COOH, —H, —COO—C$_{1-4}$ alkyl, —C$_6$H$_4$COOH, or —C$_6$H$_4$COO—C$_{1-4}$ alkyl; and yet more preferably —COOH, —H, —COOCH$_3$, —C$_6$H$_4$COOH, or —C$_6$H$_4$COOCH$_3$.

In one embodiment, A preferably represents an aryl group bound to the ortho position or the para position of the -Y-L-X group, and substituted with an electron withdrawing group, and more preferably represents an aryl group bound to the ortho position of the -Y-L-X group, and substituted with an electron withdrawing group. The aryl group is preferably a C$_{6-10}$ aryl group such as a phenyl group. The electron withdrawing group is preferably selected from the group consisting of —COOR$^8$, halo group, —OH, —NO$_2$, —CN, —CO—R$^9$, and —SO$_2$—R$^{10}$; more preferably —COOR$^8$; and even more preferably —COOH. The number of the electron withdrawing group may be one or more (for example, 2, 3, 4, or 5).

Each of R$^8$, R$^9$, and R$^{10}$ independently and preferably represents H or C$_{1-18}$ alkyl group, and more preferably represents H or C$_{1-8}$ alkyl group.

R$^1$ preferably represents a C$_{1-6}$ alkyl group, and more preferably represents a C$_{1-4}$ alkyl group such as methyl group or ethyl group.

Each of R$^2$ and R$^3$ independently and preferably represents a branched C$_{3-18}$ alkyl group or a C$_{3-7}$ cycloalkyl group. The branched C$_{3-18}$ alkyl group is exemplified by isopropyl group, isobutyl group, sec-butyl group, tert-butyl group, isopentyl group, neopentyl group, tert-pentyl group, isohexyl group, isoheptyl group, isooctyl group, 2-ethylhexyl group, isononyl group, isodecyl group, isolauryl group, isotridecyl group, isomyristyl group, isopentadecyl group, isopalmityl group, isoheptadecyl group, and isostearyl group.

R$^2$ and R$^3$, together with the carbon atom to which they are bound, typically form a ring which may be substituted with a substituent; preferably form a condensed ring, a spiro ring or a bridged ring which may be substituted with a substituent; and more preferably form a bridged ring which may be substituted with a substituent. The bridged ring preferably has 5 to 10 carbon atoms, and is exemplified by norbornane ring, cubane ring, and adamantane ring. Among these, adamantane ring is particularly preferred. The substituent is preferably halo group, and more preferably chloro group. The number of the substituent, when substituted on the ring, may be one or more (for example, 2, 3, 4, or 5).

R$^4$ preferably represents H, or a halo group, —OH, —NO$_2$, —CN, —COOH, —COO—C$_{1-18}$ alkyl, —COH, —CO—C$_{1-18}$ alkyl, —SO$_2$H, or —SO$_2$-C$_{1-18}$ alkyl bound to the ortho or the para position of the -Y-L-X group; more preferably H, or a halo group or —CN bound to ortho or the para position of the -Y-L-X group; and even more preferably H, or a halo group or —CN bound to the ortho position of the -Y-L-X group.

X preferably represents H, a trialkylsilyl group, (2,4-dinitrophenyl)sulfonyl group, a 3,4,6-trimethyl-2,5-dioxobenzyl group, 2-(3-carboxy-4-nitrophenyl)-S—S-ethyloxycarbonyl group, 4-azidobenzyloxycarbonyl group, or a group represented by formula X1, X2, X3, X4, X5, X6, or X7:

[Chemical Formula 10]

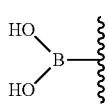
X1

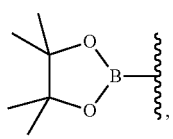
X2

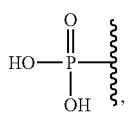
X3

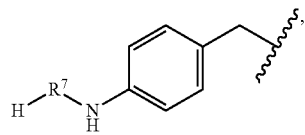
X4

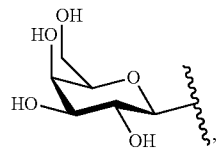
X5

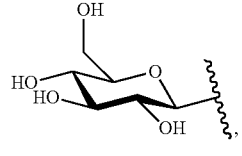
X6

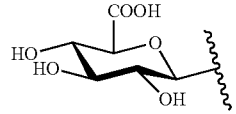
X7

(wherein,
R$^7$ represents one amino acid residue, or a group formed of a sequence of a plurality of amino acid residues, with the C-terminal of the group bound to NH, and the wavy line represents a linkage point to L).

Y, L, and X are preferably combined according to (1) to (4) below.
(1) Y represents —O— or —NH—, L is absent, and X represents H;
(2) Y represents —O— or —NH—, L is absent, and X represents a caging group, preferably a group represented by formula X3;
(3) Y represents —O— or —NH—, L represents a linker represented by formula L1, L2, L3 or L4, M represents —O— or —NH—, and X represents a caging group; and
(4) Y is absent, L is absent, and X represents a caging group, preferably a group represented by formula X1 or X2.

The compound represented by the formula [I] or a salt thereof may exist as an ion in a solution. For example, the compound or a salt thereof, having a carboxy group or a hydroxy group, may be ionized to —COO$^-$ or —O$^-$ in the solution.

In one embodiment, it is preferred that:
A represents —C≡C-E bound to the ortho position of the -Y-L-X group;
E represents —COOH, —H, —CN, —COO—C$_{1-8}$ alkyl, phenyl, —C$_6$H$_4$O—C$_{1-8}$ alkyl, —C$_6$H$_4$COOH, —C$_6$H$_4$COO—C$_{1-8}$ alkyl, 4-pyridinyl, methylpyridinium-4-yl, 3,3-dimethyl-3H-indolyl, or 1,3,3-trimethyl-3H-indol-1-ium-2-yl;
each of R$^2$ and R$^3$ independently represents a branched C$_{3-18}$ alkyl group or a C$_3$-7 cycloalkyl group, or forms, together with the carbon atom to which they are bound, a condensed ring, spiro ring or bridged ring which may be substituted by a substituent; and
R$^4$ represents H, or a halo group or —CN bound to the ortho position or the para position of the -Y-L-X group.

In one embodiment, it is preferred that:

A represents —C≡C-E bound to the ortho position of the -Y-L-X group;

E represents —COOH, —H, —CN, —COO—$C_{1-4}$ alkyl, —$C_6H_4$COOH, or —$C_6H_4$COO—$C_{1-4}$ alkyl;

$R^2$ and $R^3$ form, together with the carbon atom to which they are bound, an adamantane ring which may be substituted by a halo group; and $R^4$ represents H, or a halo group or —CN bound to the ortho position of the -Y-L-X group.

In one embodiment, it is preferred that:

A represents —C≡C-E bound to the ortho position of a -Y-L-X group;
  (i) E represents —H, Y represents —O—, L is absent, and X represents H, a trialkylsilyl group, or a group represented by formula X3; or
  (ii) E represents —COOH, Y represents —O—, L is absent, and X represents H, a trialkylsilyl group, or a group represented by Formula X3; or
  (iii) E represents —$C_6H_4$COOH, Y represents —O—, L is absent, and X represents H, a trialkylsilyl group, or a group represented by formula X3, $R^2$ and $R^3$ form, together with the carbon atom to which they are bound, an adamantane ring which may be substituted by a halo group; and $R^4$ represents H, or a halo group or —CN bound to the ortho position of the -Y-L-X group.

In one embodiment, it is preferred that:

A represents an aryl group substituted with —COOH and bound to the ortho position of the -Y-L-X group;

$R^2$ and $R^3$ form, together with the carbon atom to which they are bound, an adamantane ring which may be substituted by a halo group; and $R^4$ represents H, or a halo group or —CN bound to the ortho position of the -Y-L-X group.

The compound represented by formula [I] is preferably a compound represented by following formula [I-A], [I-B], [I-C], [I-D], [I-E], [I-F], [I-G], [I-H], [I-I], [I-J], [I-K], [I-L], [I-M], [I-N], or [I-O]:

[Chemical Formula 13]

[I-A]

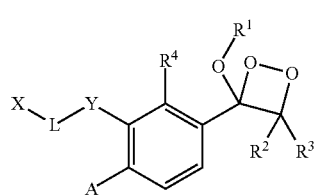

[I-B]

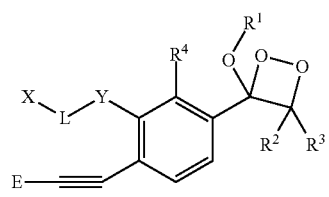

[I-C]

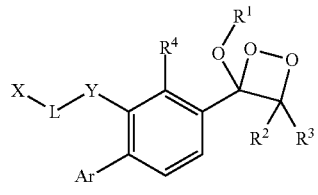

[I-D]

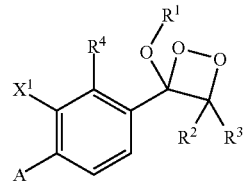

[I-E]

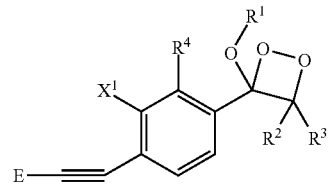

[I-F]

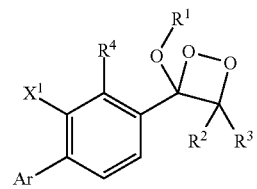

[I-G]

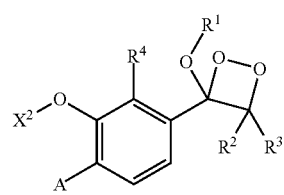

[I-H]

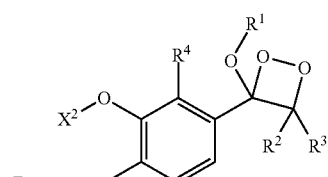

[I-I]

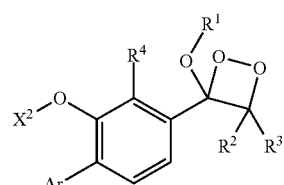

[I-J]

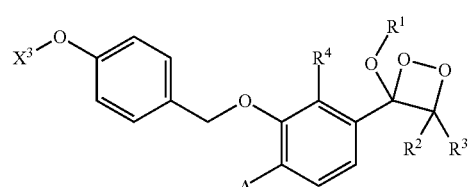

[I-K]

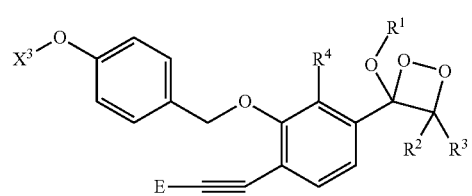

-continued

[I-L]
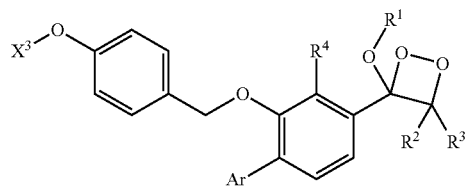

[I-M]
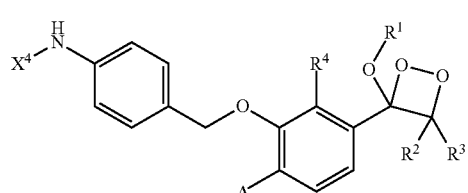

[I-N]
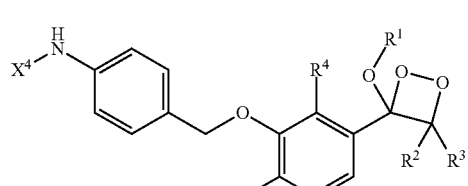

[I-O]
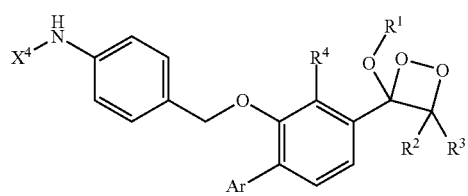

(wherein:

Ar represents an aryl group substituted with an electron withdrawing group;

$X^1$ represents a group represented by formula X1 or X2;

$X^2$ represents H, a trialkylsilyl group, or a group represented by formula X3;

$X^3$ represents H, a trialkylsilyl group, or a group represented by formula X3, X5, X6, or X7;

$X^4$ represents (2,4-dinitrophenyl)sulfonyl group, or a group represented by formula X4 in which $R^7$ is a group having an enzyme-cleavable amino acid sequence in which a plurality of amino acid residues are chained; and A, E, $R^1$, $R^2$, $R^3$, $R^4$, X, L, and Y are the same as described above).

The compound represented by the formula [I] is more preferably a compound represented by the following formula [I-P], [I-Q], [I-R] or [I-S]:

[Chemical Formula 12]

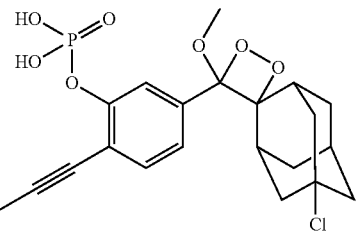

[I-P]

[I-Q]

[I-R]

[I-S]

The compound represented by Formula [I] may exist typically in the form of enantiomer, diastereomer, or racemic mixture.

The salt of the compound represented by the formula [I] may be inorganic salt or organic salt. The salt is exemplified by alkali metal salts (for example, sodium salt, potassium salt, lithium salt); alkali earth metal salt (for example, calcium salt, magnesium salt); other metal salts (for example, aluminum salt, iron salt, zinc salt, copper salt, nickel salt, cobalt salt); ammonium salt, tetramethylammonium salt, amine salts (for example, t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tris(hydroxymethyl) aminomethane salt); inorganic acid salts (for example, hydrofluoride, hydrochloride, hydrobromide, hydroiodide, nitrate, perchlorate, sulfate, phosphate); organic acid salts (for example, methanesulfonate, trifluoromethanesulfonate, ethanesulfonate, benzenesulfonate, p-toluenesulfonate, acetate, malate, fumarate, succinate, citrate, tartrate, oxalate, maleate); and amino acid salts (for example, glycine salt, lysine salt, arginine salt, ornithine salt, glutamate salt, aspartate salt).

The compound represented by formula [I] or the salt thereof may be bound to a fluorophore to form a conjugate. The fluorophore is exemplified by fluorescein dye (for example, FAM), rhodamine dye (for example, TAMRA), coumarin dye, cyanine dye, pyrene dye, and boron-dipyrromethene dye.

The compound represented by formula [I] or the salt thereof, although not particularly limited, may be produced typically according to a reaction formula below:

[Chemical Formula 13]

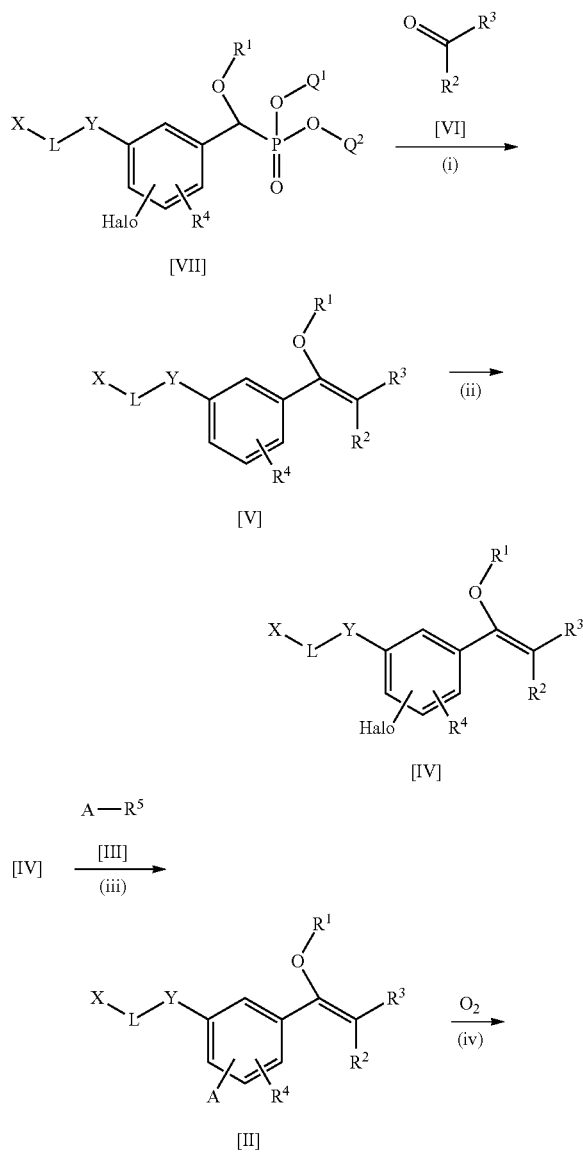

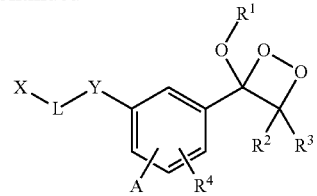

(where,

Halo represents a halo group;

$R^5$ represents H or a group represented by formula X1 or X2 (a broken line represents a linkage point with A);

each of $Q^1$ and $Q^2$ independently represents an alkyl group optionally substituted with one or more halo groups; and A, $R^1$, $R^2$, $R^3$, $R^4$, X, L, and Y are the same as described above.

Process (i) relies upon the Horner-Wazworth-Emmons reaction. Typically, a compound represented by formula [VII] is dissolved in a solvent such as alcohol, tetrahydrofuran, 1,2-dimethoxyethane, or dimethyl sulfoxide, to which a base such as sodium hydride, sodium methoxide, potassium carbonate, or n-butyllithium is added to generate an anion, and then a compound represented by formula [VI] is added so that the reaction can proceed. The reaction may proceed typically within a temperature range from −78° C. to a reflux temperature.

Process (ii) relies upon halogenation. Typically, a compound represented by formula [V] is dissolved in a solvent such as toluene, to which a halogenating agent such as N-iodosuccinimide is added so that the reaction can proceed. The reaction may proceed typically within a temperature range from 0° C. to 30° C.

Process (iii) relies upon a coupling reaction (for example, the Sonogashira coupling reaction, Suzuki coupling reaction). In a typical process of the Sonogashira coupling, a mixture of a compound represented by formula [IV], a palladium catalyst such as tetrakis(triphenylphosphine) palladium (Pd(PPh$_3$)$_4$), a copper salt such as copper(I) iodide, and a base such as isopropylamine or triethylamine (which can also serve as a solvent), is mixed with a compound represented by formula [III] whose $R^5$ representing H. The mixture may also contain a ligand such as trialkylphosphine or triarylphosphine added thereto. The reaction may proceed typically within a temperature range from 5° C. to 30° C. In a typical process of the Suzuki coupling, a compound represented by formula [IV] is reacted with a compound represented by Formula [III] whose $R^5$ representing a group represented by formula X1 or X2, typically in the presence of a palladium catalyst such as tris(dibenzylideneacetone) dipalladium (Pd$_2$(dba)$_3$), a ligand such as 2-dicyclohexylphosphino-2',6'-dimethoxybiphenyl (Sphos), and a base such as potassium phosphate. The reaction can proceed typically in a mixed solvent of water, and an organic solvent such as tetrahydrofuran, toluene, or dioxane. The reaction may proceed typically within a temperature range from 5° C. to 100° C.

Process (iv) relies upon a reaction of a compound represented by formula [II] with singlet oxygen. The reaction can proceed typically by a method in which a compound represented by formula [II] is irradiated with light in an oxygen atmosphere, in the presence of a solvent (for example, halogenated hydrocarbon such as dichloromethane, dichloroethane, carbon tetrachloride, and/or, alcohol such as methanol, ethanol), and a photosensitizer (for example, methylene blue, rose bengal, tetraphenylporphyrin). The reaction may proceed typically within a temperature range from 5 to 30° C.

In a case where the compounds to be subjected to the reaction in the individual processes typically have amino group, carboxy group, or hydroxy group, these groups may optionally be protected with a versatile protecting group which may be deprotected after the reaction. Reaction products of the individual processes may optionally be purified, typically by washing, distillation, filtration, chromatography, or recrystallization.

3. Chemiluminescence Probe

The compound represented by the formula [I] or the salt thereof may be used as a probe (hereinafter, also referred to as "chemiluminescence probe") for in vitro or in vivo detection of the analyte. In vitro detection of the analyte in the sample may typically rely upon enzyme immunoassay (EIA). In vivo detection of the analyte may rely upon a method called in vivo imaging, typically described in U.S. Patent Application Publication No. 2019/290787.

4. Composition

In one embodiment, the composition contains the compound represented by formula [I] or the salt thereof, and a solvent. The solvent may be an organic solvent or an aqueous solvent. The aqueous solvent is exemplified by water, physiological saline, and buffer solution. The buffer solution is exemplified by Good's buffers such as HEPES, TAPS, MOPS, BES, and TES; Tris-hydrochloride buffer; Owren's Veronal buffer; and imidazole hydrochloride buffer. The number of kinds of buffer substance contained in the buffer solution may be one, or two or more. Glycine may optionally be added to the buffer solution.

In the composition, the amount of the aqueous solvent is typically $10^4$ to $10^{10}$ parts by mass, per 100 parts by mass of the compound represented by formula [I] or the salt thereof, which is more preferably $10^5$ to $10^9$ parts by mass, and even more preferably $10^6$ to $10^8$ parts by mass.

The composition may further contain an additive. The additive is exemplified by surfactant and salt. Only one kind of additive may be used singly, or two or more kinds are used in a combined manner.

The composition, while demonstrating high luminous efficiency even without containing the surfactant, can demonstrate further enhanced luminous efficiency with the surfactant contained therein. The surfactant is not particularly limited as long as it can activate the surface. The surfactant may be non-ionic surfactant, anionic surfactant, cationic surfactant, or amphoteric surfactant. Among them, the non-ionic surfactant is preferred. The nonionic surfactant is exemplified by sorbitan fatty acid esters such as sorbitan monolaurate; polyoxyethylene sorbitan fatty acid esters such as Tween™-20, Tween™-40, Tween™-60, Tween™-80; glycerin fatty acid esters such as glycerin monostearate; polyoxyethylene glycerin fatty acid esters such as polyoxyethylene glyceryl monostearate; polyoxyethylene polyoxypropylene glycol such as Poloxamer 188; and polyoxyethylene alkyl phenyl ethers such as Triton™ X-100.

The amount of the surfactant is typically 10 to $10^6$ parts by mass, per 100 parts by mass of the compound represented by formula [I] or the salt thereof, which is more preferably 100 to $10^5$ parts by mass.

The salt is exemplified by chloride such as magnesium chloride, and acetate such as sodium acetate. The amount of the salt is typically 1 to $10^4$ parts by mass, per 100 parts by mass of the compound represented by formula [I] or the salt thereof, which is more preferably 10 to 1000 parts by mass.

The composition may be used for in vitro or in vivo detection of the analyte. In vitro detection of the analyte in the sample may typically rely upon EIA. In vivo detection of the analyte may rely upon a method called in vivo imaging, typically described in U.S. Patent Application Publication No. 2019/290787.

5. Chemiluminescence Method

In one embodiment, the chemiluminescence method includes reacting the compound or the salt thereof whose X representing a caging group, with the uncaging substance. The uncaging substance usable herein may be those having been described in "1. Definition". The uncaging substance is preferably an enzyme. In an exemplary case where X in formula [I] given by a caging group represented by formula X3, the uncaging substance may be alkaline phosphatase.

In the reaction, the amount of consumption of the uncaging substance may typically be $10^{-10}$ to $10^{10}$ parts by mass, per 100 parts by mass of the compound represented by formula [I] or the salt thereof, whose X representing the caging group, the proportion may preferably be $10^{-7}$ to $10^7$ parts by mass.

Temperature and time of the reaction are not particularly limited as long as the reaction can proceed. The reaction temperature may be set optimum for the enzyme, typically at 25 to 45° C. The reaction time may be set typically to 30 seconds to 3 hours, preferably 50 seconds to 2 hours, and more preferably 160 seconds to 2 hours.

6. Method for Measuring Chemiluminescence Signal

In one embodiment, the method for measuring a chemiluminescence signal includes measuring a chemiluminescence signal generated by the chemiluminescence method having been described in "5. Chemiluminescence Method". Measurement of the chemiluminescence signal in this process includes detecting presence or absence of the signal, and quantifying intensity of the signal. The chemiluminescence signal may be measured by any of known methods. More specifically, a commercially available luminometer, and a device for chemiluminescent immunoassay (CLIA), for example, may be used.

7. Reagent

The compound represented by formula [I] or the salt thereof, whose X representing the caging group, the chemiluminescence probe composed of such compound or the salt thereof, or, the composition that contains such compound or the salt thereof, may be provided as a reagent. The reagent may be suitably used for in vitro detection of the analyte. In vitro detection of the analyte in the sample may typically rely upon EIA. The chemiluminescence probe and the composition usable herein may be those having been described respectively in "3. Chemiluminescence Probe" and "4. Composition".

In the reagent, concentration of the compound represented by formula [I] or the salt thereof, whose X representing a caging group, may be appropriately set typically according to type of the analyte and assay conditions, for example to 0.01 μM to 10 mM, and preferably 0.1 μM to 1 mM.

The reagent usually contains a solvent. The solvent is exemplified by those having been described typically in "4. Composition". The reagent may contain other optional components that typically include additives such as preservative, antioxidant, and stabilizer.

8. Reagent Kit

Figure 4:
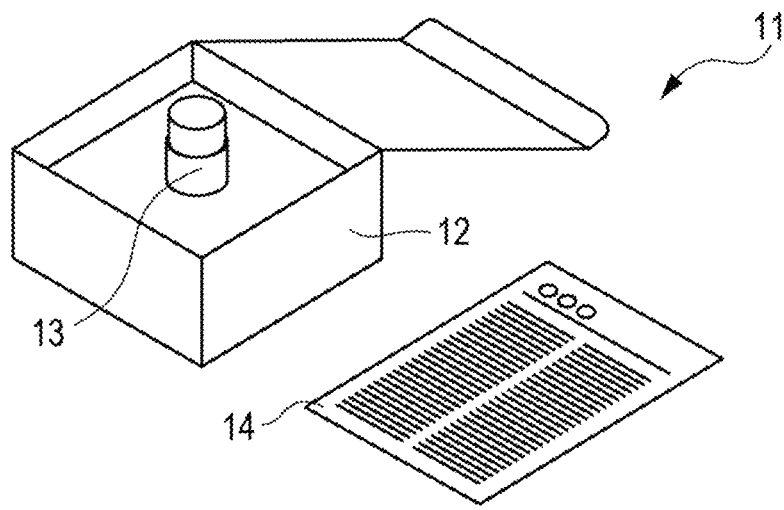
FIG. 4 illustrates an exemplary supply form of a reagent of the present disclosure.

The reagent is usually packaged in a container, and provided to the user. The container may alternatively be packaged in a box, and may be provided as a reagent kit to the user. The box may have enclosed therein a package insert that typically describes a method of using the reagent kit. FIG. 4 illustrates an exemplary supply form of the reagent kit. In a reagent kit 11, reference numeral 12 denotes a packing box, reference numeral 13 denotes the container that contains the reagent, and reference numeral 14 denotes the package insert.

Another embodiment of the reagent kit contains a first reagent that contains the compound represented by formula [I] or the salt thereof, whose X representing the caging group, a chemiluminescence probe composed of such compound or the salt thereof, or, a composition that contains such compound or the salt thereof; and a second reagent that contains the uncaging substance. The first reagent usable herein may be those having been described in "7. Reagent".

The uncaging substance in the second reagent usable herein may be those having been described in "1. Definition". Concentration of the uncaging substance may be appropriately set typically according to type of the uncaging substance and assay conditions, for example to $10^{-18}$ M to 1 M, and preferably $10^{-15}$ M to 1 M.

The second reagent usually contains a solvent. The solvent is exemplified by those having been described typically in "4. Composition". The reagent may contain other optional components that typically include additives such as preservative, antioxidant, and stabilizer.

Figure 5:
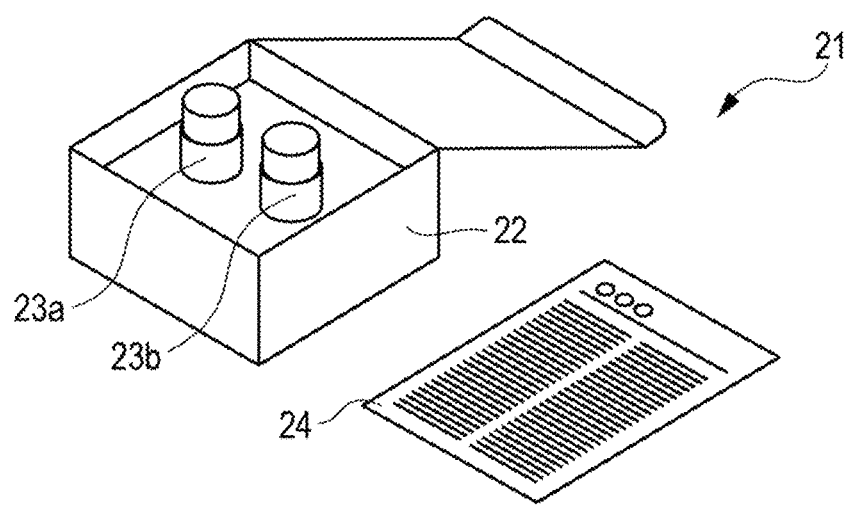
FIG. 5 illustrates an exemplary supply form of a reagent kit of the present disclosure.

The first reagent and the second reagent may be provided to the user, while being contained in separate containers and packaged in a box. The box may have enclosed therein a package insert that typically describes a method of using the reagent kit. FIG. 5 illustrates an exemplary supply form of the reagent kit. In a reagent kit 21, reference numeral 22 denotes a packing box, reference numeral 23a denotes the container that contains the first reagent, reference numeral 23b denotes the container that contains the second reagent, and reference numeral 24 denotes the package insert.

9. Method for Assaying Analyte

In one embodiment, a method for assaying an analyte in a sample includes:
    forming, on a solid phase, an immune complex that contains the analyte, a capture body that binds to the analyte, and a detector that binds to the analyte and contains an uncaging substance;
    reacting the uncaging substance in the immune complex, with the compound represented by formula [I] or the salt thereof, whose X representing a caging group, to generate a chemiluminescence signal; and
    measuring the chemiluminescence signal to assay the analyte.

The method for assaying the analyte in the sample may only be a method based on any of known immunoassay methods, wherein the method is preferably based on the enzyme-linked immunosorbent assay (ELISA method), and more preferably based on the sandwich ELISA method. Alternatively, an immune complex transfer method described in U.S. Pat. No. 5,236,849 may be used.

The solid phase used in the process of forming the immune complex, although not particularly limited, is exemplified by latex, rubber, polyethylene, polypropylene, polystyrene, styrene-butadiene copolymer, polyvinyl chloride, polyvinyl acetate, polyacrylamide, polymethacrylate, styrene-methacrylate copolymer, polyglycidyl methacrylate, acrolein-ethylene glycol dimethacrylate copolymer, polyvinylidene difluoride (PVDF), silicone, agarose, gelatin, red blood cell, silica gel, glass, inert alumina, and magnetic body. Only one kind of these materials may be used singly, or two or more kinds may be combined. Form of the solid phase is exemplified by particle, microplate, microtube, membrane, and test tube, among them particularly preferred is particle. In one embodiment, the solid phase is preferably a magnetic particle. The magnetic particle is exemplified by those containing, as a base material, $Fe_2O_3$ and/or $Fe_3O_4$, cobalt, nickel, ferrite, and magnetite.

The capture body that binds to the analyte is not particularly limited as long as it can be bound to the solid phase to capture the analyte, and may typically be antigen or antibody. The detector may bind to the analyte, and may contain the uncaging substance. The uncaging substance is exemplified by those having been described in "1. Definition", which reacts with the compound represented by formula [I] or the salt thereof, whose X representing the caging group, to generate the chemiluminescence signal. The detector is exemplified by antibody labeled with the uncaging substance.

Assuming the analyte as antibody A, then an antigen functions as the capture body for capturing the antibody A. Assuming that the sample contains the antibody A, then an obtainable immune complex contains the sample, an antigen, and a detection antibody B. The complex may be formed on the solid phase, by contacting a solution that contains the immune complex, with the solid phase on which the antigen may be immobilized. The immune complex may be formed on the solid phase, alternatively by contacting the solid phase having the antigen preliminarily immobilized thereon, the sample, and the detection antibody.

Mode of immobilization of the capture body on the solid phase is not specially limited. For example, the capture body and the solid phase may be directly bonded, or may be indirectly bonded while placing other substance in between. The direct bonding is exemplified by physical adsorption, and covalent bond with use of a linking agent. The indirect bonding typically relies upon combination of biotins (including biotin, and biotin analogs such as desthiobiotin and oxybiotin) and avidins (including avidin, and avidin analogs such as streptavidin, tamavidin™); and combination of hapten and anti-hapten antibody (for example, a compound having 2,4-dinitrophenyl group (DNP group), and an anti-DNP antibody). In one embodiment, the capture body may be immobilized on the solid phase, via a bond between the biotins and avidins, with use of the capture body preliminarily modified with biotins, and the solid phase having avidins preliminarily bound thereto.

B/F (bound/free) separation, for removing any free component that remains unreacted without forming the complex, may be interposed between the formation of the immune complex and the detection of the chemiluminescence signal. The free component that remains unreacted refers to a component that does not constitute the immune complex. This is exemplified by the capture body and the detector that remained unbound to the analyte. With the solid phase given as a particle, the B/F separation may rely upon centrifugation, although the technique for the separation is not specifically limited. With the solid phase given as a container such as a microplate or a microtube, the B/F separation may rely upon removal of a liquid that contains the unreacted free component. With the solid phase given as a magnetic particle, the B/F separation may rely upon removal of a liquid that contains the unreacted free component, under suction through a nozzle, while magnetically restraining the magnetic particle with use of a magnet. The method is preferred from the viewpoint of automatization. After removing the unreacted free component, the solid phase having the complex bound thereon may be washed with suitable aqueous medium such as PBS.

In the process of generating the chemiluminescent signal, the uncaging substance is preferably reacted with the compound represented by formula [I] or the salt thereof, whose X representing the caging group, while controlling the amount of consumption of the former typically to $10^{-10}$ to $10^{10}$ parts by mass, and preferably to $10^{-7}$ to $10^{7}$ parts by mass, per 100 parts by mass of the latter.

The process of measuring the chemiluminescence signal may rely upon the method having been described in "6. Method for Measuring Chemiluminescence Signal".

EXAMPLES

The present invention will be further detailed referring to Examples, to which the present invention is by no means limited.

Exemplary Synthesis

Reference Example 1

[Chemical Formula 14]

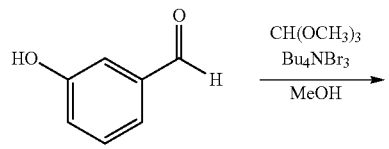

Trimethyl orthoformate (130 g, 1.22 mol) and tetrabutylammonium tribromide (Bu$_4$NBr$_3$) (15.0 g, 0.03 mol) were added to a solution of 3-hydroxybenzaldehyde (50.0 g, 0.41 mol) in 500 mL of methanol (MeOH), and the mixture was stirred overnight at room temperature. The reaction mixture was poured into water, and extracted twice with ethyl acetate. The organic layer was washed with saturated brine, dried over sodium sulfate, and the solvent was then evaporated under reduced pressure to obtain 3-(dimethoxymethyl) phenol as a yellow liquid (75.0 g, quant.).

$^1$HNMR (CDCl$_3$, 400 MHz): δ7.21-7.25 (m, 1H), 6.99-7.01 (m, 2H), 6.85-6.87 (m, 1H), 5.36 (s, 1H), 3.35 (s, 6H).

Reference Example 2

[Chemical Formula 15]

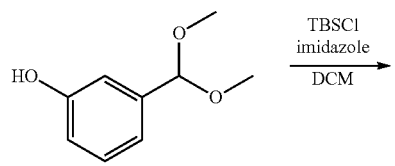

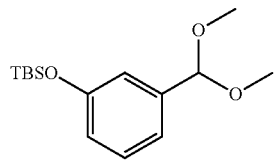

tert-Butyldimethylchlorosilane (TBSCl) (74.1 g, 0.49 mol) was added to a solution of the compound of Reference Example 1 (75.0 g) and imidazole (41.8 g, 0.61 mol) in 750 mL of dichloromethane (DCM), and the mixture was stirred at room temperature for one hour. The reaction mixture was poured into water, and extracted twice with dichloromethane. The organic layer was washed with saturated brine, dried over sodium sulfate, and the solvent was then evaporated under reduced pressure to obtain a crude product. The crude product was purified by silica gel chromatography (petroleum ether/ethyl acetate=50:1 to 20:1), to obtain tert-butyl (3-(dimethoxymethyl)phenoxy)dimethylsilane as a colorless liquid (80.0 g, 69% (2 steps)).

$^1$HNMR (CDCl$_3$, 400 MHz): δ7.23 (t, J=8.0 Hz, 1H), 7.04 (d, J=7.6 Hz, 1H), 6.96 (s, 1H), 6.80 (dd, J=2.0, 8.0 Hz, 1H), 5.39 (s, 1H), 3.33 (s, 9H), 1.00 (s, 6H), 0.21 (s, 6H).

Reference Example 3

[Chemical Formula 16]

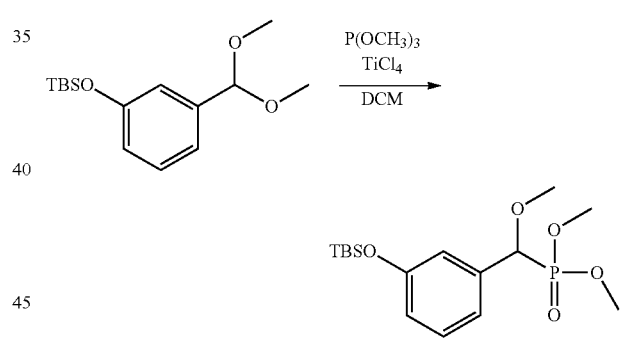

A solution of the compound of Reference Example 2 (80.0 g, 0.28 mol) and trimethyl phosphite (52.7 g, 0.42 mol) in 800 mL of dichloromethane was cooled to 0° C., to which titanium(IV) chloride (80.5 g, 0.42 mol) was added dropwise. The reaction mixture was stirred at 0° C. for one hour. The reaction mixture was poured into water, and extracted twice with dichloromethane. The organic layer was washed with saturated brine, dried over sodium sulfate, and the solvent was then evaporated under reduced pressure to obtain a crude product. The crude product was purified by silica gel chromatography (petroleum ether/ethyl acetate=30:1 to 10:1), to obtain dimethyl((3-((tert-butyldimethylsilyl)oxy)phenyl)(methoxy)methyl)phosphonate as a colorless liquid (57.0 g, 56%).

$^1$HNMR (CDCl$_3$, 400 MHz): δ7.24 (t, J=8.0 Hz, 1H), 7.03 (d, J=7.2 Hz, 1H), 6.96 (d, J=2.0 Hz, 1H), 6.83 (d, J=8.4 Hz, 1H), 4.50 (d, J=15.6 Hz, 1H), 3.66-3.73 (m, 6H), 3.39 (s, 3H), 0.99 (s, 9H), 0.21 (s, 6H).

Reference Example 4

[Chemical Formula 17]

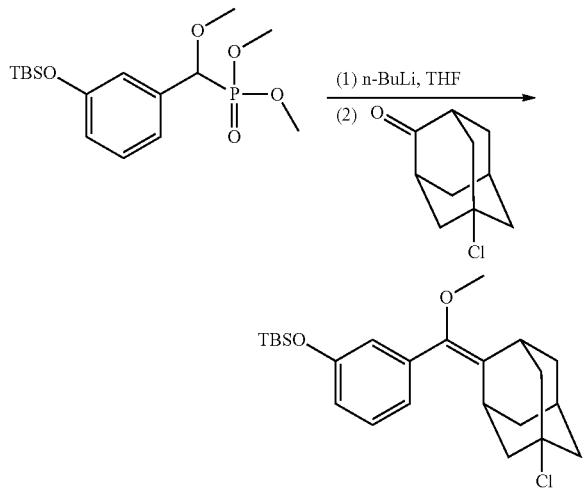

A solution of the compound of Reference Example 3 (57.0 g, 0.16 mol) in 570 mL of anhydrous tetrahydrofuran (THF) was cooled to −78° C., to which n-butyllithium (n-BuLi) (2.5 M, 110 mL, 0.28 mol) was added in a nitrogen atmosphere. The reaction mixture was stirred in the nitrogen atmosphere, at −78° C. for one hour. A solution of 5-chloro-2-adamantanone (35.0 g, 0.19 mol) in 150 mL of anhydrous tetrahydrofuran was added dropwise at −78° C. The reaction mixture was stirred in the nitrogen atmosphere, at −78° C. for 30 minutes. The reaction mixture was poured into a saturated aqueous ammonium chloride solution, and extracted twice with ethyl acetate. The organic layer was washed with saturated brine, dried over sodium sulfate, and the solvent was then evaporated under reduced pressure to obtain a crude product. The crude product was purified by silica gel chromatography (petroleum ether/ethyl acetate=30:1 to 10:1), to obtain tert-Butyl(3-((Z)-((1R,3S,5S,7S)-5-chloroadamantan-2-ylidene)(methoxy)methyl)phenoxy)dimethylsilane as a colorless liquid (30.0 g, 45%).

$^1$HNMR (CDCl$_3$, 400 MHz): δ7.23 (t, J=8.0 Hz, 1H), 6.90 (d, J=7.6 Hz, 1H), 6.78-6.83 (m, 2H), 3.46 (s, 1H), 3.30 (s, 3H), 2.79 (s, 1H), 2.16-2.28 (m, 7H), 1.71-1.85 (m, 4H), 1.00 (s, 9H), 0.22 (s, 6H).

Reference Example 5

[Chemical Formula 18]

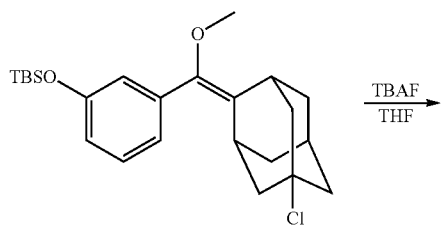

-continued

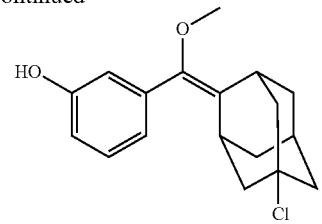

A solution of the compound of Reference Example 4 (30.0 g, 71.6 mmol) in 300 mL of tetrahydrofuran was cooled to 0° C., to which a solution of tetrabutylammonium fluoride (TBAF) in 80 mL of tetrahydrofuran (1 M, 80 mmol) was added. The reaction mixture was stirred at 0° C. for 30 minutes. The reaction mixture was poured into water, and extracted twice into ethyl acetate. The organic layer was washed with saturated brine, dried over sodium sulfate, and the solvent was then evaporated under reduced pressure to obtain 3-((Z)-((1R,3S,5S,7S)-5-chloroadamantan-2-ylidene)(methoxy)methyl)phenol as a colorless liquid (24 g, quant.).

$^1$HNMR (CDCl$_3$, 400 MHz): δ7.21-7.25 (m, 1H), 6.81-6.86 (m, 3H), 3.45 (s, 1H), 3.32 (s, 3H), 2.81 (s, 1H), 2.15-2.30 (m, 7H), 1.85-1.86 (m, 1H), 1.71-1.79 (m, 3H).

Reference Example 6

[Chemical Formula 19]

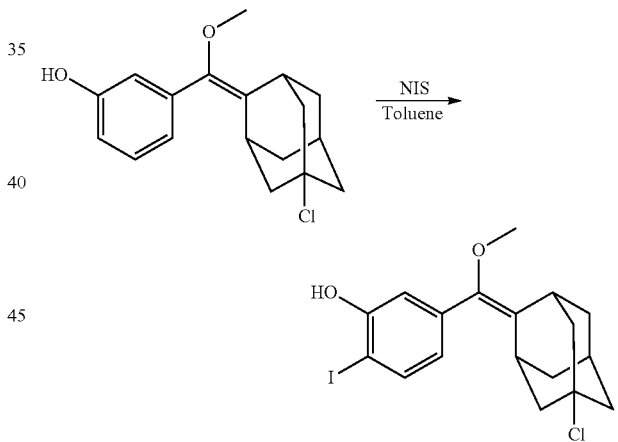

A solution of the compound of Reference Example 5 (24 g) in 500 mL of toluene was cooled to 0° C., to which N-iodosuccinimide (NIS) (17.7 g, 78.6 mmol) was added. The reaction mixture was stirred at room temperature for one hour. The reaction mixture was poured into water, and extracted twice with ethyl acetate. The organic layer was washed with saturated brine, dried over sodium sulfate, and the solvent was then evaporated under reduced pressure to obtain a crude product. The crude product was purified by silica gel chromatography (petroleum ether/ethyl acetate=20:1 to 3:1), to obtain 5-((Z)-((1R,3S,5S,7S)-5-chloroadamantan-2-ylidene)(methoxy)methyl)-2-iodophenol as a white solid (9.3 g, 30% (two steps)).

$^1$HNMR (CDCl$_3$, 400 MHz): δ7.66 (d, J=8.0 Hz, 1H), 6.94 (d, J=1.6 Hz, 1H), 6.64 (dd, J=1.6, 8.0 Hz, 1H), 5.41 (s, 1H), 3.45 (s, 1H), 3.31 (s, 3H), 2.80 (s, 1H), 2.15-2.27 (m,

7H), 1.85-1.86 (m, 1H), 1.71-1.78 (m, 3H). Mass calcd.: 430; MS found: 431 [M+H]⁺.

Reference Example 7

[Chemical Formula 20]

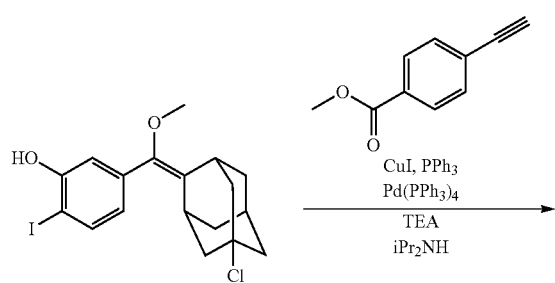

Reference Example 8

[Chemical Formula 21]

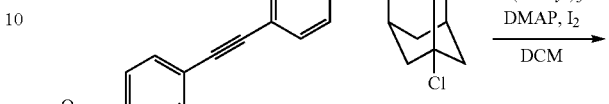

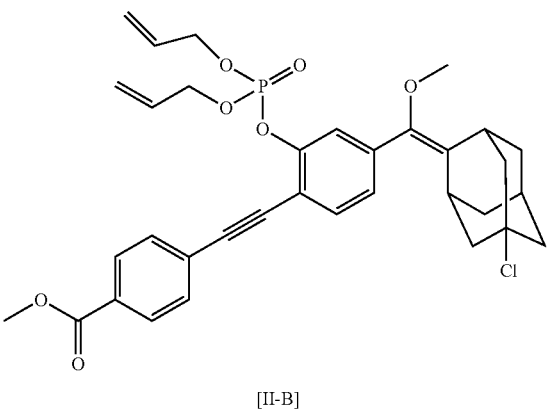

The compound of Reference Example 6 (430.7 mg, 1.0 mmol, 1 eq.), tetrakis(triphenylphosphine) palladium(0) (Pd(PPh₃)₄) (115.6 mg, 0.1 mmol, 0.1 eq.), copper(I) iodide (38.1 mg, 0.2 mmol, 0.2 eq.), triphenylphosphine (PPh₃) (52.5 mg, 0.2 mmol, 0.2 eq.), diisopropylamine (iPr₂NH) (2 mL), and triethylamine (TEA) (4 mL) were mixed, and the mixture was stirred in an argon atmosphere, at room temperature for 30 minutes. Methyl 4-ethynylbenzoate (320.4 mg, 2.0 mmol, 2 eq.) was added, and the mixture was stirred at 80° C. for one hour. After cooled down to room temperature, the reaction mixture was diluted with dichloromethane, and filtered through celite pad. The organic layer was washed with 1N hydrochloric acid, water, and saturated brine, dried over sodium sulfate, and the solvent was then evaporated under reduced pressure to obtain a crude product. The crude product was purified by silica gel chromatography (n-hexane/ethyl acetate=4:1) to obtain a compound represented by formula [II-A] as a yellow solid (222.4 mg, 48%).

ESI-MS m/z:461[M−H]⁻.

A solution of triallyl phosphite (P(O-Allyl)₃) (71.6 µL, 0.51 mmol, 6 eq.) in 2 mL of anhydrous dichloromethane was cooled to 0° C., to which iodine (108.5 mg, 0.43 mmol, 5 eq.) was added. The reaction liquid was stirred at 0° C. for 5 minutes, and then returned to room temperature. The mixture was added dropwise at room temperature, to a solution of the compound of Reference Example 7 (39.6 mg, 0.09 mmol, 1 eq.) and DMAP (62.7 mg, 0.51 mmol, 6 eq.) in 2 mL of anhydrous dichloromethane. The mixture was stirred at room temperature for 40 minutes, then diluted with dichloromethane, the organic layer was washed with saturated aqueous ammonium chloride solution, saturated aqueous sodium hydrogen carbonate solution, and saturated brine, dried over sodium sulfate, and the solvent was then evaporated under reduced pressure to obtain a crude product. The crude product was purified by silica gel chromatography (n-hexane/ethyl acetate=3:1) to obtain a compound represented by formula [II-B] as a red liquid (28.7 mg, 55%).

ESI-MS m/z: 624[M+H]⁺.

Reference Example 9

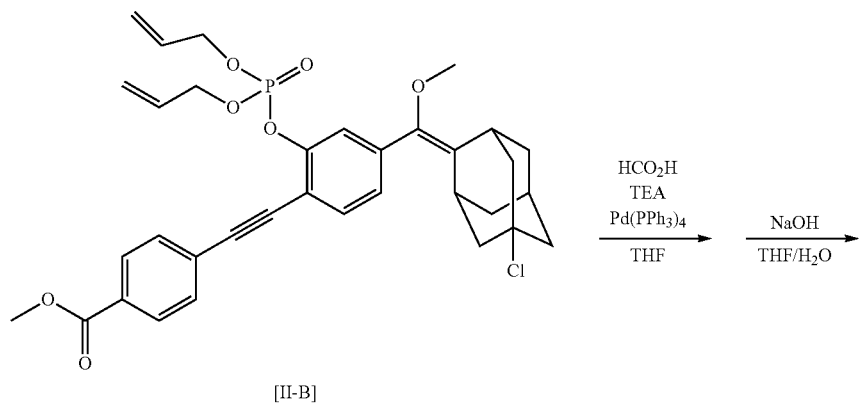

[II-B]

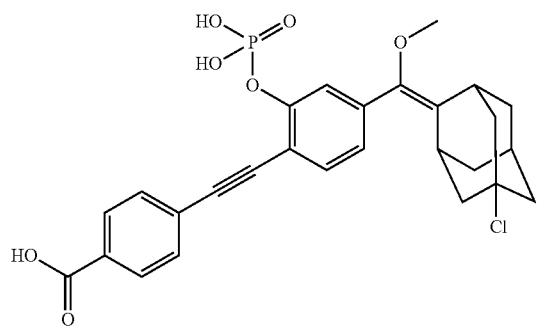

[II-C]

Formic acid (38.5 µL, 1.02 mmol, 5 eq.), triethylamine (34.1 µL, 0.24 mmol, 1.2 eq.) and tetrakis(triphenylphosphine) palladium(0) (23.6 mg, 0.02 mmol, 0.1 eq.) were added to a solution of the compound of Reference Example 8 (127.1 mg, 0.20 mmol, 1 eq.) in 3 mL of tetrahydrofuran, and the mixture was stirred at 50° C. for one hour. After cooled down to room temperature, the solvent was evaporated under reduced pressure. Resultant residue was dissolved in tetrahydrofuran (4 mL) and 1 N aqueous sodium hydroxide solution (1 mL), and the mixture was stirred at room temperature for one hour. The solvent was evaporated under reduced pressure, and the residue was purified by silica gel chromatography (dichloromethane/methanol=10:1 to 3:1) to obtain a compound represented by formula [II-C] as a yellow solid (160.4 mg, quant.).

ESI-MS m/z: 527[M−H]−.

Example 1

[Chemical Formula 23]

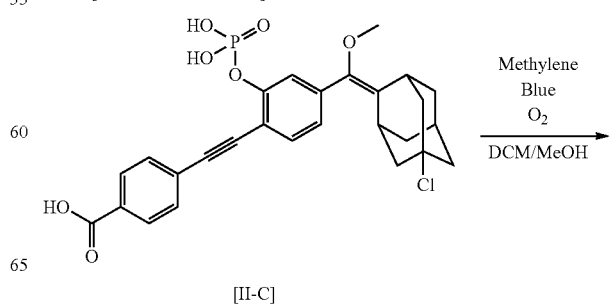

[II-C]

-continued

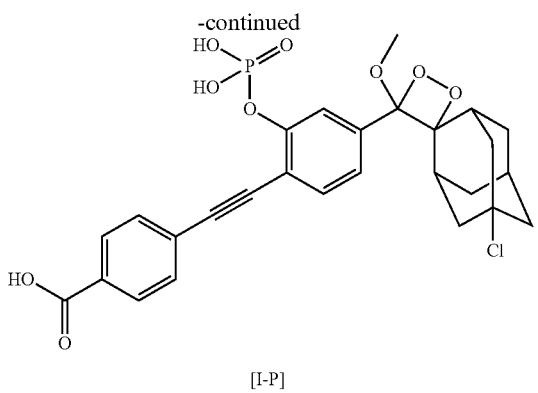

[I-P]

The compound of Reference Example 9 (60.8 mg, 0.12 mmol, 1 eq.) and methylene blue (2 mg) were dissolved in dichloromethane (2 mL)/methanol (0.5 mL), and the mixture was stirred in an oxygen atmosphere for 45 minutes, under irradiation of light (LED, 25 W, 5000 K). The reaction mixture was purified by silica gel chromatography (ethyl acetate/methanol=1:1) to obtain a crude product. The crude product was purified by HPLC (eluent A: water, 5 mM aqueous ammonium carbonate solution, eluent B: acetonitrile, A/B=90/10 to 10/90 (20 minutes)), to obtain a compound represented by formula [I-P] as a white solid (8.6 mg, 13%).

ESI-MS m/z: 559[M−H]⁻.

Reference Example 10

[Chemical Formula 24]

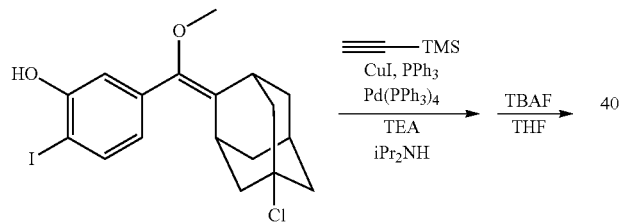

The compound of Reference Example 6 (1.29 g, 3.0 mmol, 1 eq.), tetrakis(triphenylphosphine) palladium(0) (173.3 mg, 0.15 mmol, 0.05 eq.), copper(I) iodide (57.1 mg, 0.3 mmol, 0.1 eq.), triphenylphosphine (78.7 mg, 0.3 mmol, 0.1 eq.), diisopropylamine (5 mL), and triethylamine (10 mL) were mixed, and the mixture was stirred in an argon atmosphere, at room temperature for 30 minutes. Trimethylsilylacetylene (1.24 mL, 9.0 mmol, 3 eq.) was added, and the mixture was stirred at 90° C. for 2 hours. After cooled down to room temperature, the reaction mixture was diluted with dichloromethane, and filtered through celite pad. The organic layer was washed with saturated aqueous ammonium chloride solution and saturated brine, dried over sodium sulfate, and the solvent was then evaporated under reduced pressure to obtain a crude product. The crude product was dissolved in tetrahydrofuran (15 mL), to which tetrabutylammonium fluoride solution (1 M, in tetrahydrofuran) was added. After 20-minute stirring at room temperature, the solvent was evaporated under reduced pressure. Resultant residue was purified by silica gel chromatography (n-hexane/ethyl acetate=4:1) to obtain a compound represented by formula [II-D] as a brown solid (820.2 mg, 83%).

ESI-MS m/z:327[M−H]⁻.

Reference Example 11

[Chemical Formula 25]

A solution of the compound of Reference Example 10 (32.9 mg, 0.1 mmol, 1 eq.) and dehydrated pyridine (169.2 μL, 2.10 mmol, 21 eq.) in 5 mL of dehydrated dichloromethane was cooled to 0° C., to which phosphoryl chloride (93.2 μL, 1.0 mmol, 10 eq.) was added dropwise. The mixture was stirred in an argon atmosphere at 0° C. for 3.5 hours, and the solvent was evaporated under reduced pressure. Addition of toluene and removal of the solvent under reduced pressure were repeated twice, to obtain a crude product. The crude product was purified by HPLC (eluent A: water, 5 mM aqueous ammonium carbonate solution, eluent B: acetonitrile, A/B=90/10 to 10/90 (20 minutes)), to obtain a compound represented by formula [II-E] as a white solid (17.1 mg, 42%).

ESI-MS m/z: 407[M−H]⁻.

Example 2

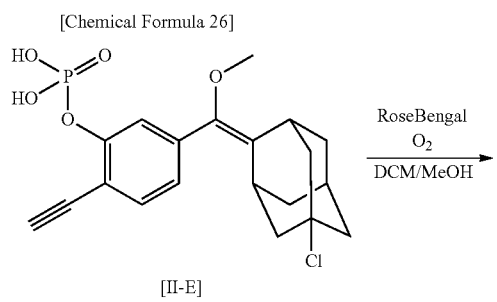

[II-E]

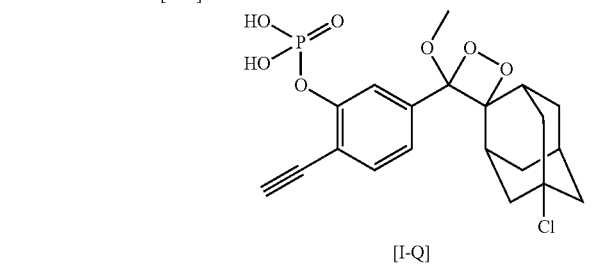

[I-Q]

The compound of Reference Example 11 (14 mg, 0.027 mmol, 1 eq.) and rose bengal B bound to polystyrene (20 mg) were added to dichloromethane (2 mL)/methanol (0.5 mL), and the mixture was stirred in an oxygen atmosphere for one hour, under irradiation of light (LED, 25 W, 5000 K). The reaction liquid was filtered through a cotton plug, and the solvent was then evaporated under reduced pressure, to obtain a crude product. The crude product was purified by HPLC (eluent A: water, 5 mM aqueous ammonium carbonate solution, eluent B: acetonitrile, A/B=90:10 to 10:90 (20 minutes)), to obtain a compound represented by formula [I-Q] as a white solid (4.5 mg, 30%).

ESI-MS m/z: 439[M−H]$^-$.

Reference Example 12

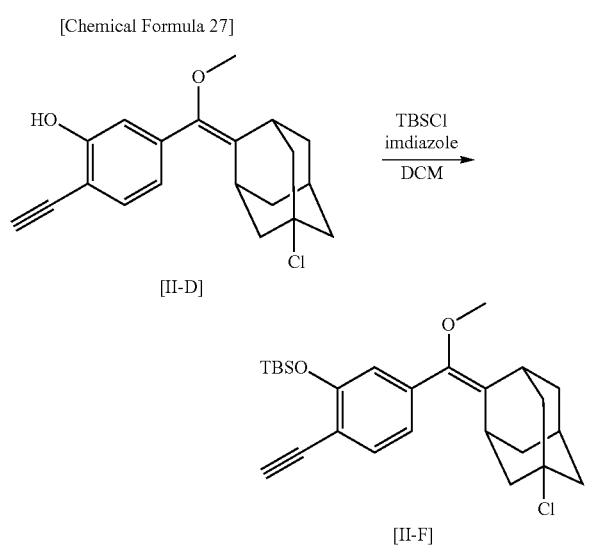

[II-D]

[II-F]

tert-Butyldimethylchlorosilane (420.5 mg, 2.8 mmol, 1.5 eq.) was added to a solution of the compound of Reference Example 10 (611.7 mg, 1.86 mmol, 1 eq.) and imidazole (253.3 mg, 3.72 mmol, 2 eq.) in 19 mL of dichloromethane. The reaction mixture was stirred in an argon atmosphere, at room temperature for 30 minutes. Imidazole (126 mg, 1.86 mmol, 1 eq.) and tert-butyldimethylchlorosilane (210 mg, 1.4 mmol, 0.7 eq.) were added to the reaction mixture, and the mixture was stirred at room temperature for 4 hours. The reaction mixture was filtered, and the filtrate was evaporated off under reduced pressure to obtain a residue. The residue was purified by silica gel chromatography (n-hexane/ethyl acetate=20:1) to obtain a compound represented by formula [II-F] as a colorless liquid (720.6 mg, 87%).

ESI-MS m/z: 443[M+H]$^+$.

Reference Example 13

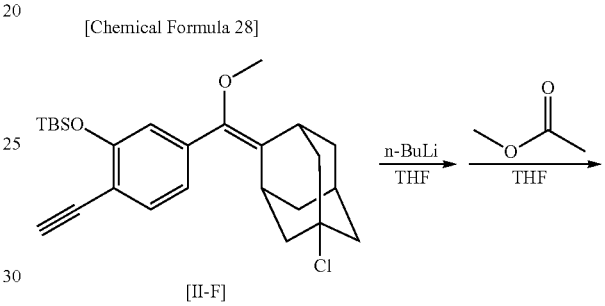

[II-F]

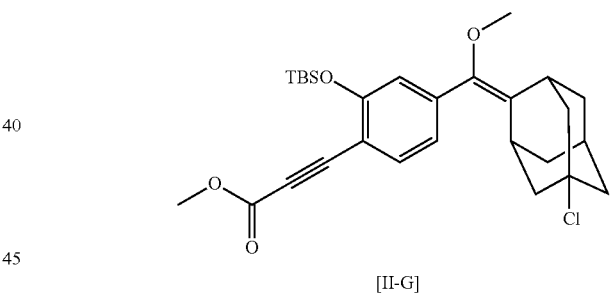

[II-G]

A solution of the compound of Reference Example 12 (680.5 mg, 1.54 mmol, 1 eq.) in 8 mL of dehydrated tetrahydrofuran was cooled to −78° C., to which n-butyllithium solution in n-hexane (2.6 M, 1.77 mL, 4.61 mol, 3 eq.) was added dropwise in a nitrogen atmosphere. The reaction mixture was stirred in the nitrogen atmosphere, at −78° C. for 30 minutes. Methyl chloroformate (589.9 μL, 7.68 mmol, 5 eq.) was added, and the mixture was stirred at room temperature for one hour. A saturated aqueous ammonium chloride solution was slowly added, the mixture was extracted twice with ethyl acetate, and washed with water and saturated brine. After drying over sodium sulfate, the solvent was evaporated under reduced pressure, to obtain a residue. The residue was purified by silica gel chromatography (n-hexane/ethyl acetate=20:1) to obtain a compound represented by formula [II-G] as a pale yellow liquid (774.1 mg, quant.).

ESI-MS m/z: 501[M+H]$^+$

Reference Example 14

[Chemical Formula 29]

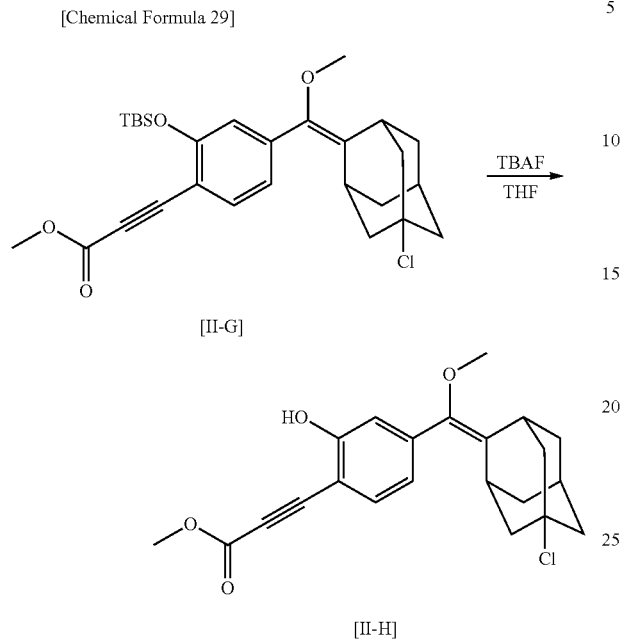

A solution of tetrabutylammonium fluoride in 1.8 mL of tetrahydrofuran (1 M, 1.8 mmol, 1.2 eq.) was added to a solution of the compound of Reference Example 13 (751.6 mg, 1.50 mmol, 1 eq.) in 7.5 mL of tetrahydrofuran, and the mixture was stirred at room temperature for 20 minutes. The reaction mixture was poured into a saturated aqueous ammonium chloride solution, and extracted twice with ethyl acetate. The organic layer was washed with saturated brine, dried over sodium sulfate, and the solvent was then evaporated under reduced pressure to obtain a residue. The residue was purified by silica gel chromatography (n-hexane/ethyl acetate=3:1) to obtain a compound represented by formula [II-H] as a white solid (456.3 mg, 79%).

ESI-MS m/z: 385[M+H]$^-$.

Reference Example 15

[Chemical Formula 30]

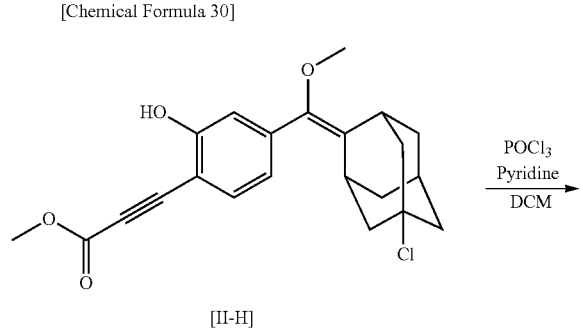

A solution of the compound of Reference Example 14 (50.3 mg, 0.13 mmol, 1 eq.) and dehydrated pyridine (219.9 μL, 2.73 mmol, 21 eq.) in 2.6 mL of dehydrated dichloromethane was cooled to 0° C., to which phosphoryl chloride (121.2 μL, 1.3 mmol, 10 eq.) was added dropwise. The mixture was stirred in an argon atmosphere at 0° C. for 40 minutes, and the solvent was then evaporated under reduced pressure. Addition of toluene and removal of the solvent under reduced pressure were repeated twice, to obtain a residue. The residue was suspended in water (2 mL), to which potassium hydroxide (218.8 mg, 3.9 mmol, 30 eq.) was added, and the mixture was stirred at room temperature for 5 minutes. The reaction mixture was purified by HPLC (eluent A: water, 5 mM aqueous ammonium carbonate solution, eluent B: acetonitrile, A/B=90:10 to 10:90 (20 minutes)), to obtain a compound represented by formula [II-J] as a white solid (36.6 mg, 62%).

ESI-MS m/z: 451[M−H]$^-$.

Example 3

[Chemical Formula 31]

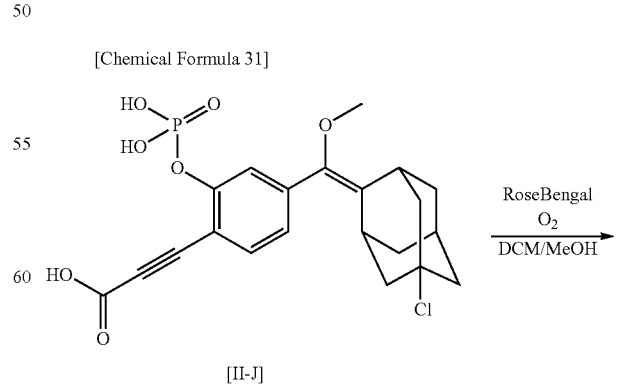

-continued

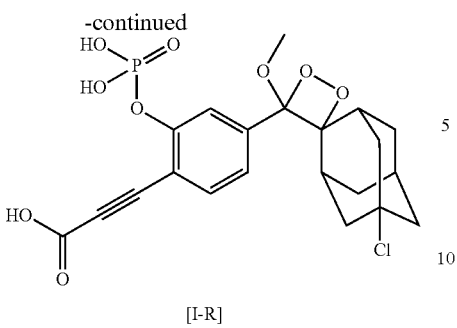

[I-R]

The compound of Reference Example 15 (36.6 mg, 0.081 mmol, 1 eq.) and rose bengal B bound to polystyrene (30 mg) were added to dichloromethane (5 mL)/methanol (2 mL), and the mixture was stirred in an oxygen atmosphere for 2 hours, under irradiation of light (LED, 25 W, 5000 K). The reaction liquid was filtered through a cotton plug, and the solvent was then evaporated under reduced pressure, to obtain a crude product. The crude product was purified by HPLC (eluent A: water, 5 mM aqueous ammonium carbonate solution, eluent B: acetonitrile, A/B=90/10 to 10/90 (20 minutes)), to obtain a compound represented by formula [I-R] as a white solid (18.4 mg, 47%).

ESI-MS m/z: 483[M−H]⁻.

Reference Example 16

[Chemical Formula 32]

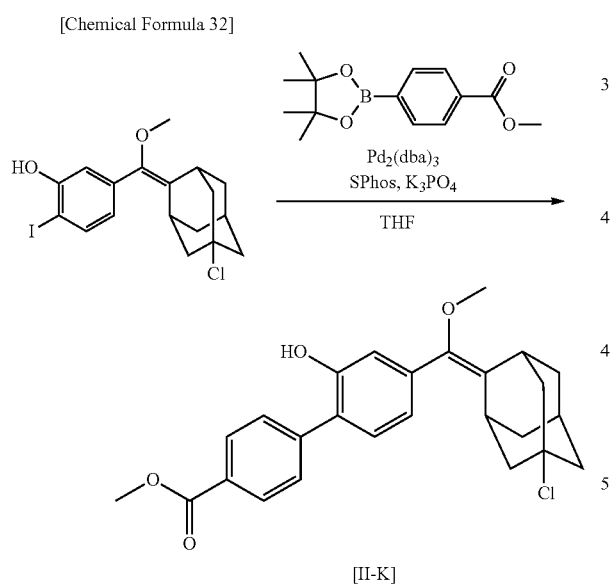

[II-K]

The compound of Reference Example 6 (215.4 mg, 0.50 mmol, 1 eq.), methyl 4-(4,4,5,5-tetramethyl-1,3,2-dioxaborolane-2-yl) benzoate (196.6 mg, 0.75 mmol, 1.5 eq), tris(dibenzylideneacetone) dipalladium(0) (Pd₂(dba)₃) (22.9 mg, 0.03 mmol, 0.05 eq.), SPhos (20.5 mg, 0.05 mmol, 0.1 eq.), potassium phosphate (212.3 mg, 1.00 mmol, 2 eq.), tetrahydrofuran (2 mL) and water (0.5 mL) were mixed, and the mixture was stirred in an argon atmosphere, at room temperature for 28 hours. The reaction mixture was diluted with ethyl acetate, the organic layer was washed with saturated aqueous ammonium chloride solution and saturated brine, dried over sodium sulfate, and the solvent was then evaporated under reduced pressure to obtain a crude product. The crude product was purified by silica gel chromatography (n-hexane/ethyl acetate=3:1) to obtain a compound represented by formula [11-K] as a white solid (163.9 mg, 75%).

ESI-MS m/z:439[M−H]⁺.

Reference Example 17

[Chemical Formula 33]

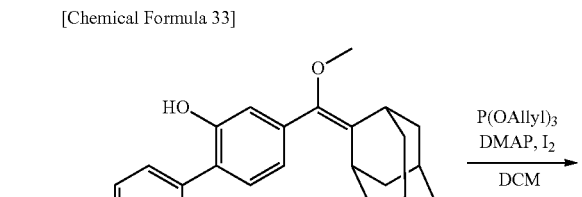

[II-K]

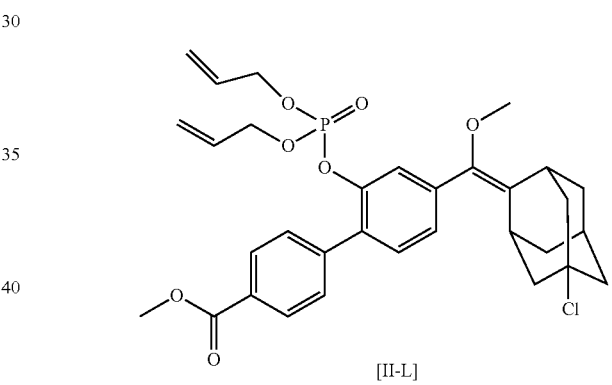

[II-L]

A solution of triallyl phosphite (96.1 µL, 0.69 mmol, 2.5 eq.) in 2 mL of anhydrous dichloromethane was cooled to 0° C., to which iodine (139.9 mg, 0.55 mmol, 2 eq.) was added. The mixture was stirred at 0° C. for 5 minutes, the temperature was returned back to room temperature, to which a solution of the compound of Reference Example 7 (121.9 mg, 0.28 mmol, 1 eq.) and DMAP (101.0 mg, 0.83 mmol, 3 eq.) in 3 mL of anhydrous dichloromethane was added dropwise at room temperature. The mixture was stirred at room temperature for 2 hours, then diluted with dichloromethane, the organic layer was washed with 1N hydrochloric acid, saturated aqueous sodium hydrogen carbonate solution and saturated brine, dried over sodium sulfate, and the solvent was then evaporated under reduced pressure to obtain a crude product. The crude product was purified by silica gel chromatography (n-hexane/ethyl acetate=3:1) to obtain a compound represented by formula [II-L] (114.1 mg, 69%).

ESI-MS m/z: 599[M+H]⁺.

Reference Example 18

[Chemical Formula 34]

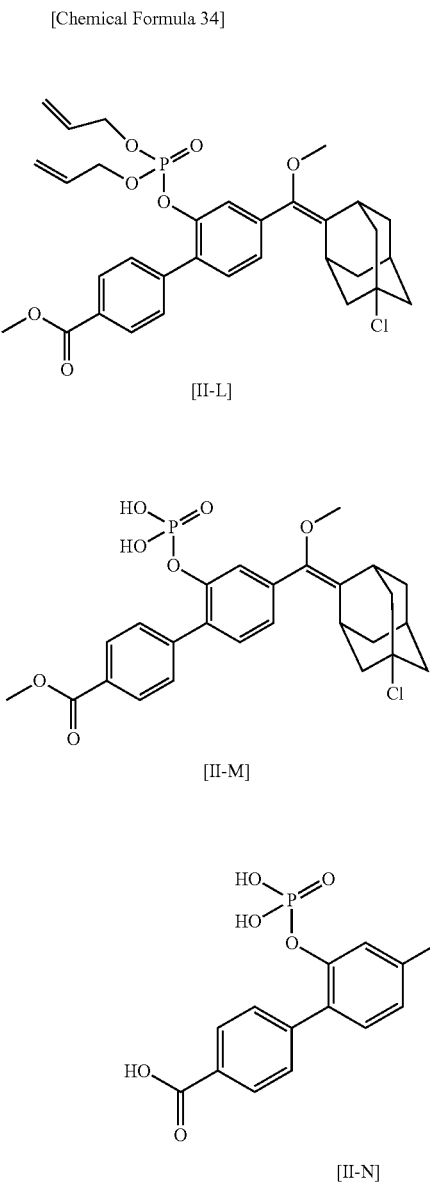

Formic acid (19.0 μL, 0.50 mmol, 5 eq.), triethylamine (16.9 μL, 0.12 mmol, 1.2 eq.) and tetrakis(triphenylphosphine) palladium(0) (11.7 mg, 0.01 mmol, 0.1 eq.) were added to a solution of the compound of Reference Example 17 (60.4 mg, 0.10 mmol, 1 eq.) in 2 mL of tetrahydrofuran, and the mixture was stirred at 60° C. for 10 minutes. After cooled down to room temperature, the solvent was evaporated under reduced pressure. Resultant residue was dissolved in tetrahydrofuran (3 mL) and 1 N aqueous sodium hydroxide solution (0.5 mL), and stirred at room temperature for one hour. The solvent was evaporated off under reduced pressure, and the residue was purified by silica gel chromatography (ethyl acetate/methanol=4:1 to 1:1) to obtain a compound represented by formula [II-N] as a white solid (44.1 mg, 87%).

ESI-MS m/z: 503[M−H]⁻.

Example 4

[Chemical Formula 35]

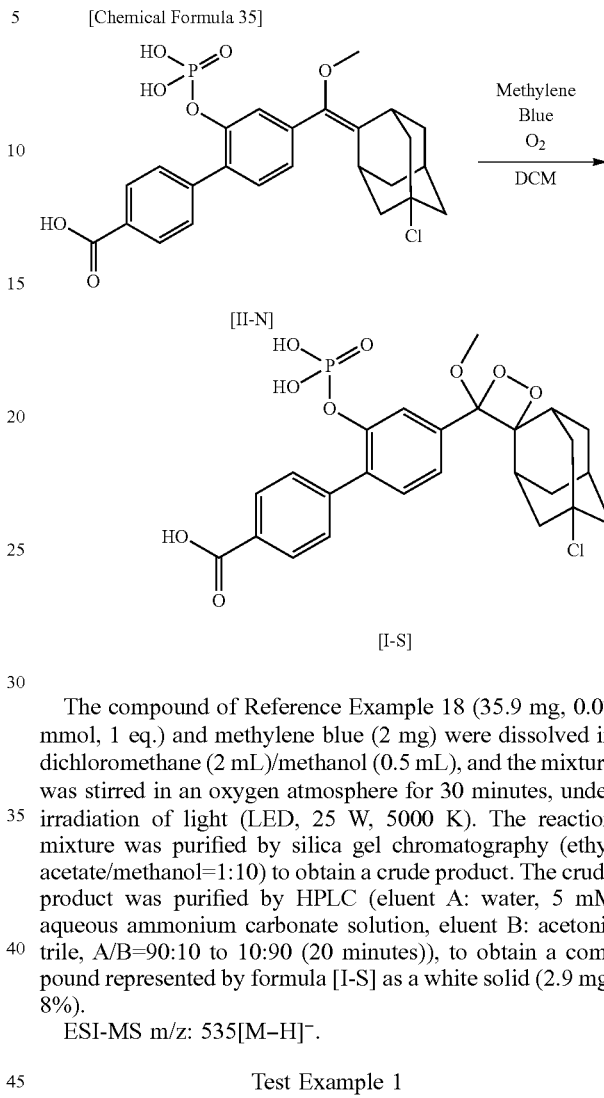

The compound of Reference Example 18 (35.9 mg, 0.07 mmol, 1 eq.) and methylene blue (2 mg) were dissolved in dichloromethane (2 mL)/methanol (0.5 mL), and the mixture was stirred in an oxygen atmosphere for 30 minutes, under irradiation of light (LED, 25 W, 5000 K). The reaction mixture was purified by silica gel chromatography (ethyl acetate/methanol=1:10) to obtain a crude product. The crude product was purified by HPLC (eluent A: water, 5 mM aqueous ammonium carbonate solution, eluent B: acetonitrile, A/B=90:10 to 10:90 (20 minutes)), to obtain a compound represented by formula [I-S] as a white solid (2.9 mg, 8%).

ESI-MS m/z: 535[M−H]⁻.

Test Example 1

A solution of 1,2-dioxetane derivative (Examples 1 to 4, Comparative Examples 1 and 2) in 5 μL of dimethyl sulfoxide (1 mM) was added to 155 μL of the reaction liquid, and the mixture was kept at 42° C. for one hour. Twenty μL of a solution containing 1 pmol of alkaline phosphatase was added, the luminescence signal was measured at 42° C. for 10 hours, and an integrated value was estimated. The reaction liquid used herein was a 2:1 mixture of a buffer solution (pH 9.6) that contains magnesium chloride and Sapphire-II™ Enhancer (from Thermo Fischer Scientific Inc.), and HISCL R4 reagent (from Sysmex Corporation).

Figure 1B:
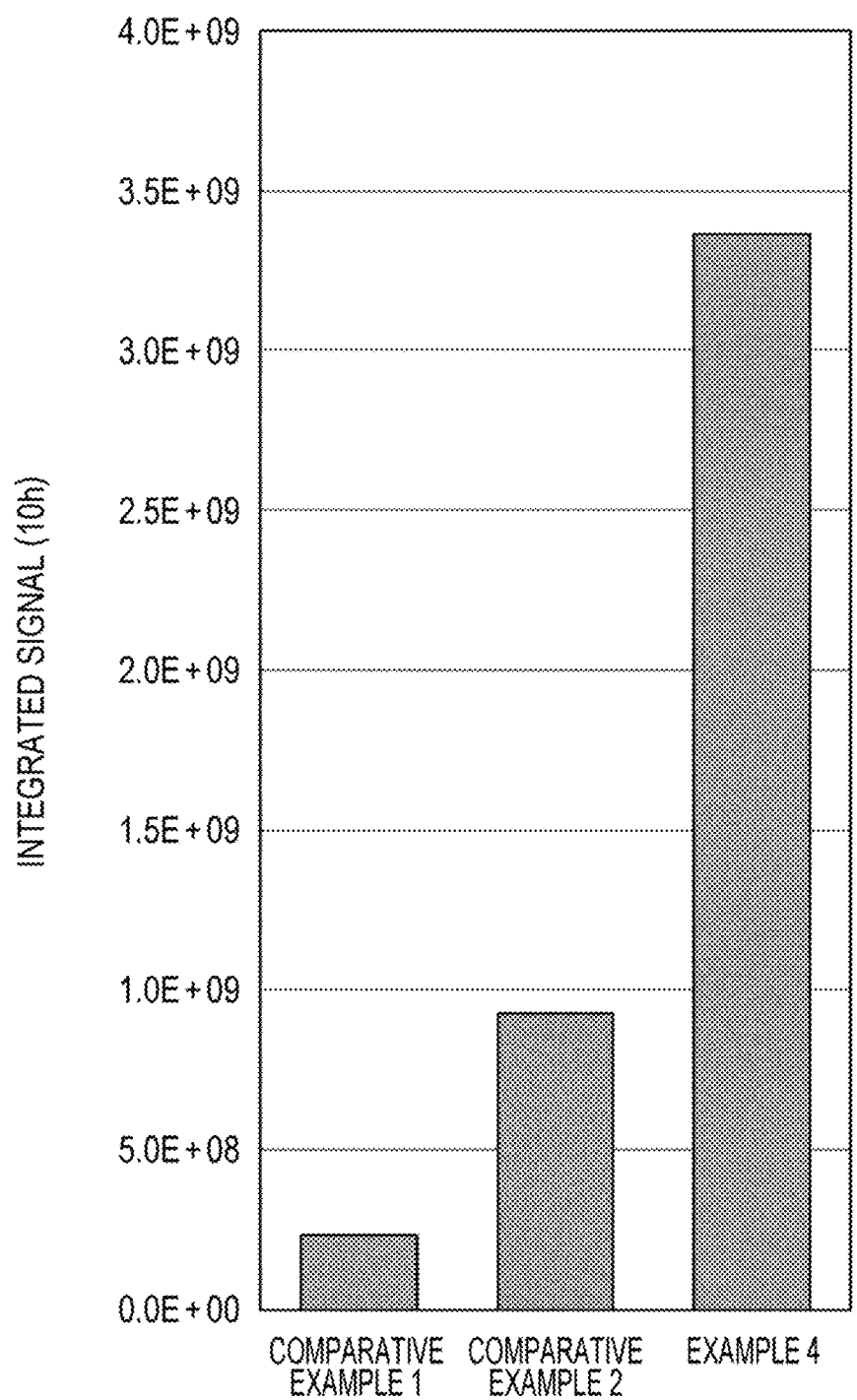
FIG. 1B is a graph comparing luminous efficiency of Example 4, with luminous efficiency of Comparative Examples 1 and 2.
Figure 2A:
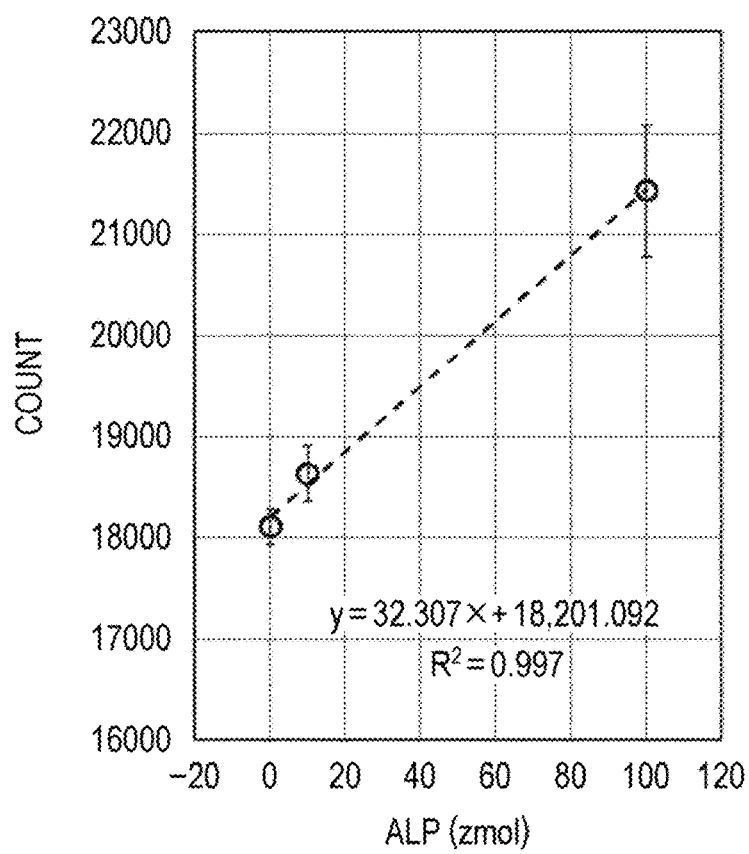
FIG. 2A is a graph illustrating a relationship between amount of alkaline phosphatase and luminescence signal in Example 1.
Figure 2B:
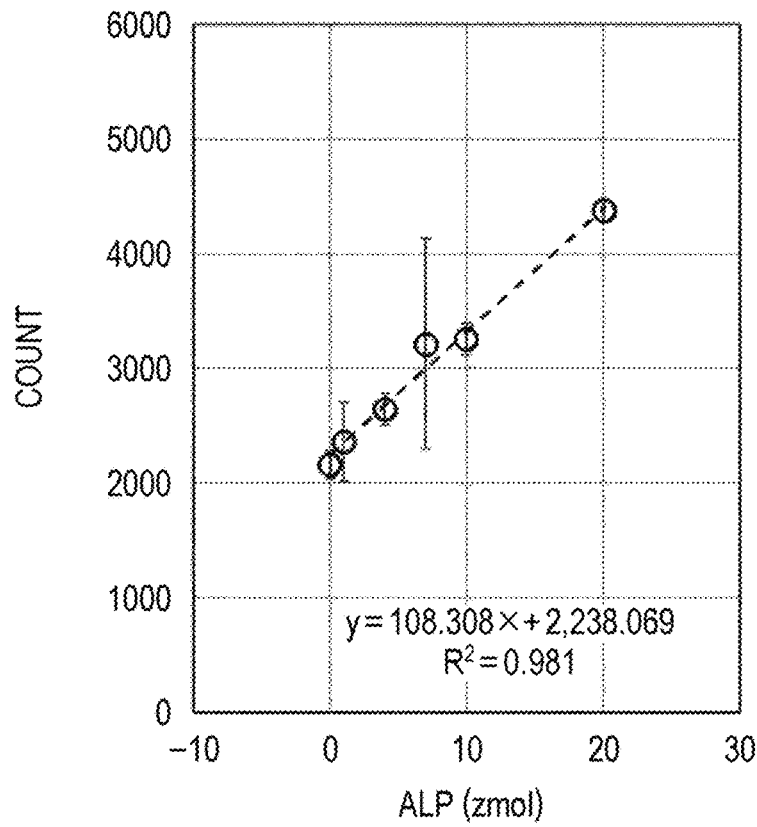
FIG. 2B is a graph illustrating a relationship between amount of alkaline phosphatase and luminescence signal in Example 2.
Figure 2C:
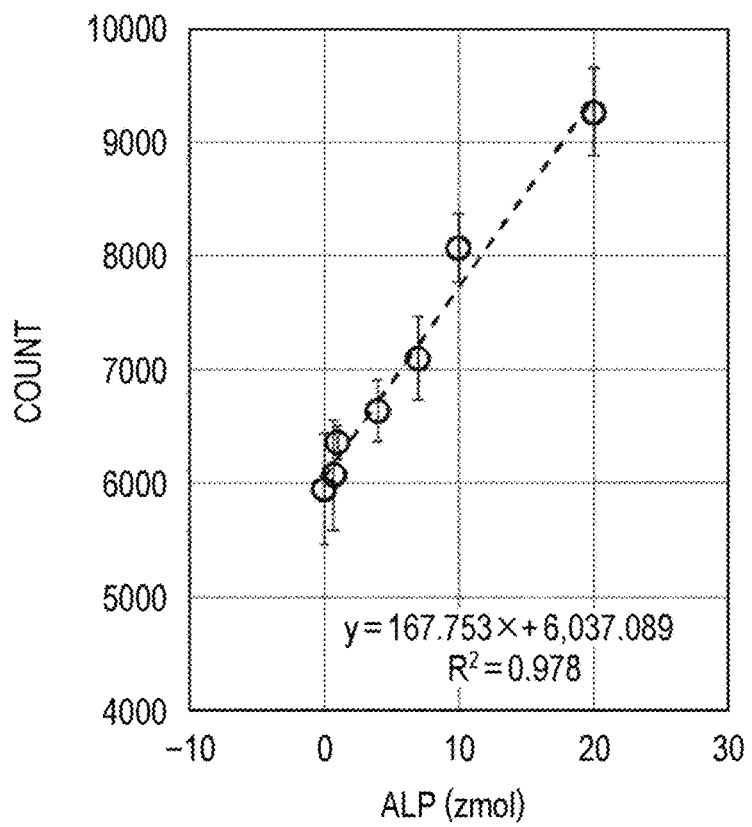
FIG. 2C is a graph showing a relationship between the amount of alkaline phosphatase and luminescence signal in Example 3 (Sapphire-II (trademark) Enhancer added)
Figure 2D:
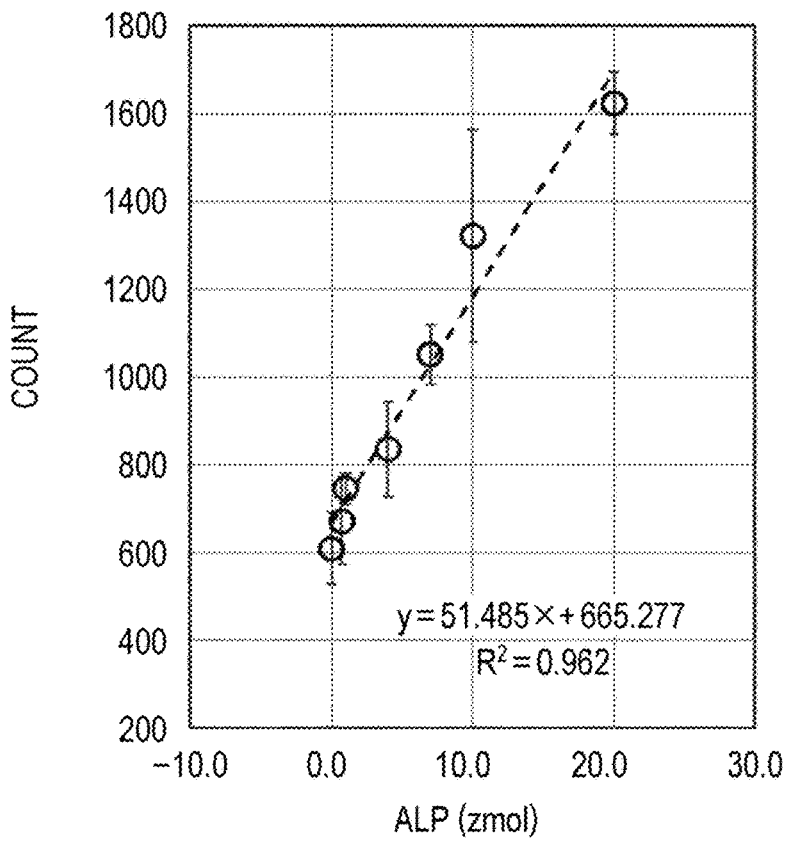
FIG. 2D is a graph illustrating the relationship between the amount of alkaline phosphatase and luminescence signal in Example 3 (Sapphire-II (trademark) Enhancer not added)
Figure 2E:
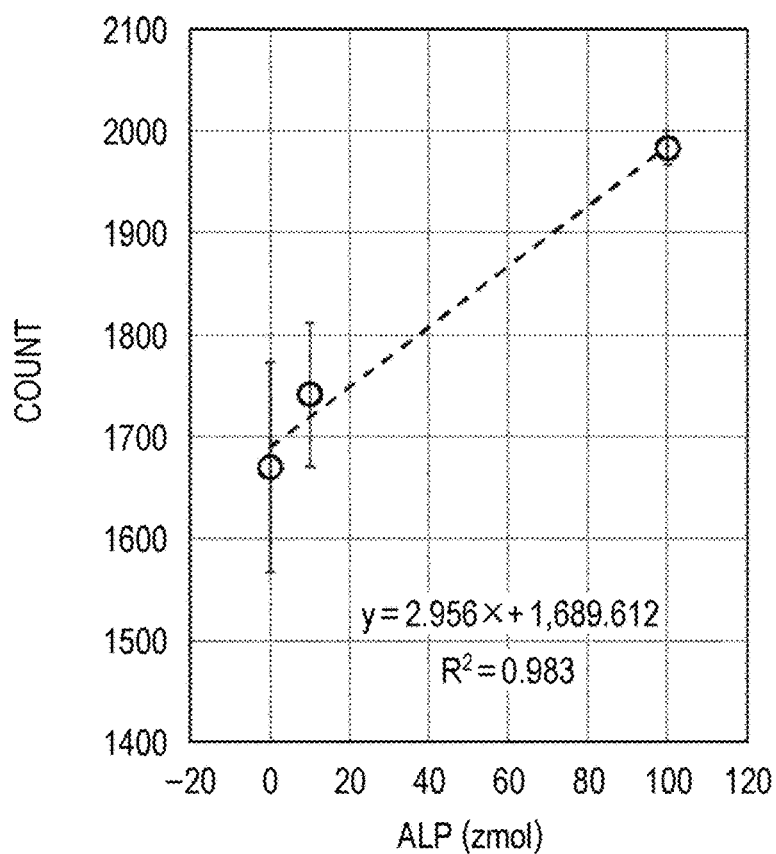
FIG. 2E is a graph illustrating a relationship between amount of alkaline phosphatase and luminescence signal in Example 4.

Results of Test Example 1 are illustrated in FIGS. 1A and 1B. As illustrated in FIGS. 1A and 1B, Examples 1 to 4 demonstrated higher chemiluminous efficiency as compared with Comparative Example 1 (CDP-Star™) and Comparative Example 2 (AquaSpark™).

Test Example 2

A solution of 1,2-dioxetane derivative (Examples 1 to 4) in dimethyl sulfoxide was added to 155 μL of the reaction liquid, and the mixture was kept at 42° C. for one hour. Twenty μL of a solution containing alkaline phosphatase was added, the mixture was incubated at 42° C. for 5 minutes, and then the chemiluminescence intensity was measured. The reaction liquid used herein was a 2:1 mixture of a buffer solution (pH 9.6) that contains magnesium chloride and Sapphire-II™ Enhancer (from Thermo Fischer Scientific Inc.), and HISCL R4 reagent (from Sysmex Corporation). In Example 3, two types of sample were prepared, a sample (S(+)) with Sapphire-II™ Enhancer added thereto, and a sample (S (+)) without such additive.

Limit of Detection (LOD) for Examples 1 to 4 was summarized in Table 1. As illustrated in FIGS. 2A to 2E, measured values of the count were found to depend on the concentration of alkaline phosphatase.

TABLE 1

|  | LOD (zmol) |
| --- | --- |
| Example 1 | 10 |
| Example 2 | 4 |
| Example 3 (S (+)) | 7 |
| Example 3 (S (−)) | 1 |
| Example 4 | 100 |

Test Example 3

After a lapse of several hours under the conditions of Test Example 1, the samples were measured with use of a spectrofluorometer F-7000 (from Hitachi High-Tech Science Corporation), to find maximum emission wavelength.

The maximum emission wavelength of Examples 1 to 4 was summarized in Table 2.

TABLE 2

|  | Maximum emission wavelength (nm) |
| --- | --- |
| Example 1 | 498 |
| Example 2 | 468 |
| Example 3 | 475 |
| Example 4 | 493 |

Test Example 4

HISCL™ HBsAg calibrator (from Sysmex Corporation) was measured with use of an automated high-sensitive Immunoassay system for research applications HI-1000 (from Sysmex Corporation), and a hepatitis B virus surface antigen kit HISCL™ HBsAg reagent (from Sysmex Corporation). For the measurement in Example 3, a sample prepared by diluting a solution of 1,2-dioxetane derivative (Example 3) in dimethylsulfoxide with a buffer solution (pH 9.6) that contains magnesium chloride (final concentration in Example 3: 93 μM), keeping the mixture at 42° C. for one hour under a light-shielding condition, and by returning the mixture to room temperature, in place of using the HISCL R4 reagent. The buffer did not contain Sapphire-II™ Enhancer (from Thermo Fischer Scientific Inc.).

Figure 3:
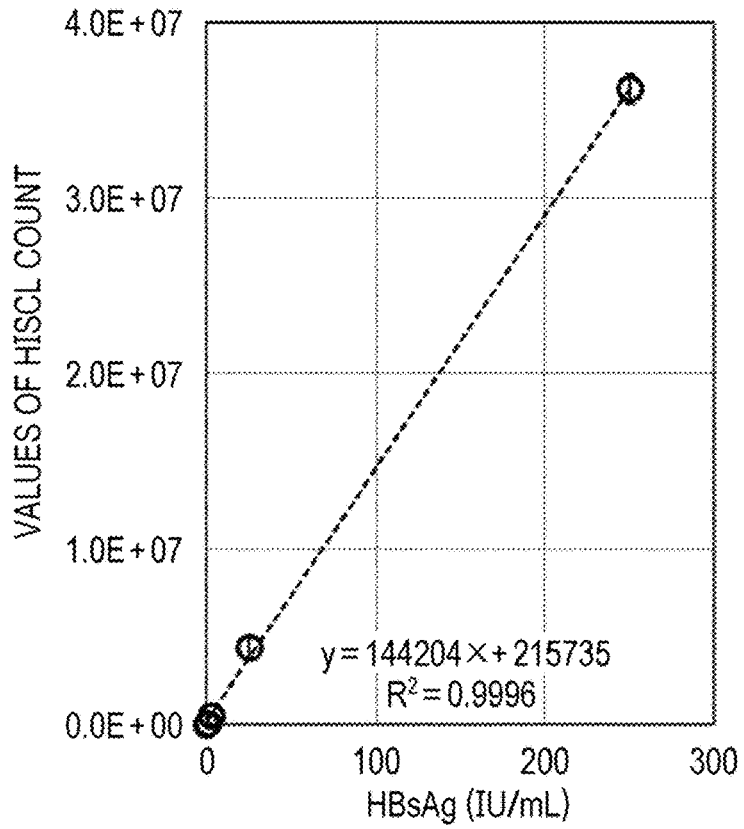
FIG. 3 is a graph illustrating results of immunoassay of hepatitis B virus surface antigen (HBsAg), with use of Example 3 (Sapphire-II (trademark) Enhancer not added)

As illustrated in FIG. 3, the measured values of the HISCL count were found to depend on the concentration of HBsAg.

What is claimed is:

1. A compound represented by formula I, or a salt thereof:

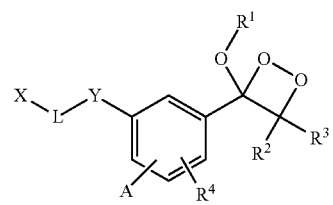

I where, $R^1$ represents a $C_{1-8}$ alkyl group, $R^2$ and $R^3$ together with the carbon atom to which they are bound, form an adamantane ring optionally substituted with a halo group;

X represents H or a caging group;

L is absent or represents a linker represented by formula L1, L2, L3, or L4:

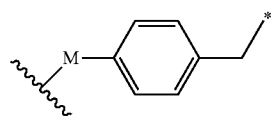

L1

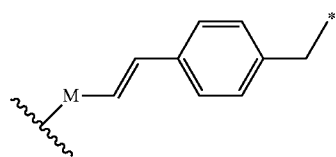

L2

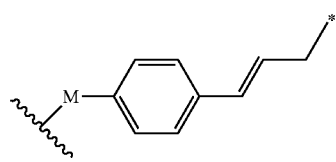

L3

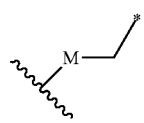

L4 in each formula,

M is absent or represents —O— or —NH—, a wavy line represents a linkage point to X, an asterisk represents a linkage point to Y;

a benzene ring in formulae L1, L2, and L3 may be substituted with a substituent selected from the group consisting of halo group, alkyl group, cycloalkyl group, and alkoxy group;

Y is absent or represents —O— or —NH—;

$R^4$ represents H or an electron withdrawing group bound to an ortho or a para position of the -Y-L-X group;

A represents —C≡C-E where, E represents —COOH, —H, —CN, —COO-alkyl, or, an aryl group, a pyridinyl group, a pyridinium group, a 3H-indolyl group, or a 3H-indol-1-ium group, optionally substituted with a substituent, or an aryl group substituted with an electron withdrawing group.

2. The compound or the salt thereof according to claim 1, wherein A is bound to an ortho position or the para position of the -Y-L-X group.

3. The compound or the salt thereof according to claim 1, wherein A represents —C≡C-E bound to an ortho position of the -Y-L-X group.

4. The compound or the salt thereof according to claim 1, wherein E represents —COOH, —H, —CN, —COO—$C_{1-8}$ alkyl, phenyl, —$C_6H_4O$—$C_{1-8}$ alkyl, —$C_6H_4COOH$, —$C_6H_4COO$—$C_{1-8}$ alkyl, 4-pyridinyl, methylpyridinium-4-yl, 3,3-dimethyl-3H-indolyl, or 1,3,3-trimethyl-3H-indol-1-ium-2-yl.

5. The compound or the salt thereof according to claim 1, wherein A represents an aryl group bound to an ortho position of the -Y-L-X group,
the aryl group is substituted with an electron withdrawing group selected from the group consisting of —$COOR^8$, halo group, —OH, —$NO_2$, —CN, —CO—$R^9$, and —$SO_2$—$R^{10}$,
and each of $R^8$, $R^9$, and $R^{10}$ independently represents H or a $C_{1-18}$ alkyl group.

6. The compound or the salt thereof according to claim 1, wherein A represents a phenyl group bound to an ortho position of the -Y-L-X group,
the phenyl group is substituted with an electron withdrawing group selected from the group consisting of —$COOR_8$, halo group, —OH, —$NO_2$, —CN, —CO—$R^9$, and —$SO_2$—$R^{10}$,
and each of $R^8$, $R^9$, and $R^{10}$ independently represents H or a $C_{1-8}$ alkyl group.

7. The compound or the salt thereof according to claim 1, wherein $R^4$ represents H, or a halo group or —CN bound to an ortho position or the para position of the -Y-L-X group.

8. The compound or the salt thereof according to claim 1, wherein $R^4$ represents H, or a halo group or —CN bound to an ortho position of the -Y-L-X group.

9. The compound or the salt thereof according to claim 1, wherein X represents H, trialkylsilyl group, (2,4-dinitrophenyl) sulfonyl group, 3,4,6-trimethyl-2,5-dioxobenzyl group, 2-(3-carboxy-4-nitrophenyl)-S-S-ethyloxycarbonyl group, 4-azidobenzyloxycarbonyl group, or a group represented by formula X1, X2, X3, X4, X5, X6, or X7:

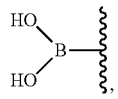
X1

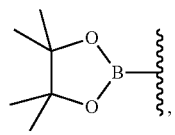
X2

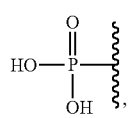
X3

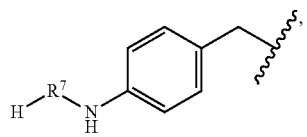
X4

-continued

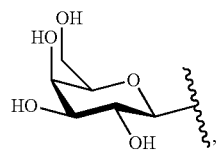
X5

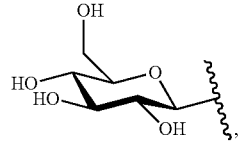
X6

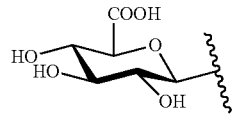
X7 wherein,
$R^7$ represents one amino acid residue, or a group formed of a sequence of a plurality of amino acid residues, with a C-terminal of the group bound to NH, and the wavy line represents a linkage point to L.

10. The compound or the salt thereof according to claim 1, satisfying any one of (1) to (4) below:
(1) Y represents —O— or —NH—, L is absent, and X represents H;
(2) Y represents —O— or —NH—, L is absent, and X represents a group represented by formula X3:

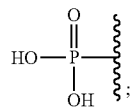
X3

(3) Y represents —O— or —NH—, L represents a linker represented by formula L1, L2, L3 or L4, M represents —O— or —NH—, and X represents a caging group; or
(4) Y is absent, L is absent, and X represents a group represented by formula X1 or X2:

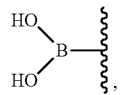
X1

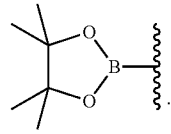
X2

11. A composition comprising:
a compound represented by formula I, or a salt thereof:

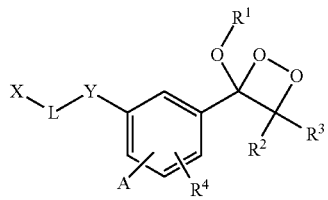

where,
$R^1$ represents a $C_{1-8}$ alkyl group,
each of $R^2$ and $R^3$ independently represents a $C_{3-18}$ alkyl group or a $C_{3-7}$ cycloalkyl group;
$R^1$ and $R^2$, $R^1$ and $R^3$, or $R^2$ and $R^3$, together with a carbon atom to which they are bound, may form an optionally substituted ring;
X represents a caging group;
L is absent or represents a linker represented by formula L1, L2, L3, or L4:

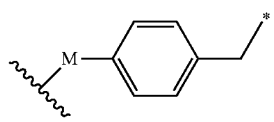

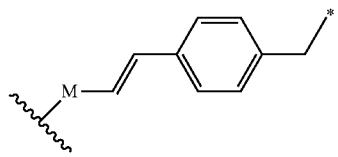

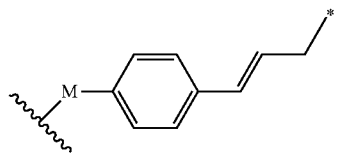

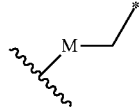

in each formula,
M is absent or represents —O— or —NH—,
a wavy line represents a linkage point to X,
an asterisk represents a linkage point to Y;
a benzene ring in formulae L1, L2, and L3 may be substituted with a substituent selected from the group consisting of halo group, alkyl group, cycloalkyl group, and alkoxy group;
Y is absent or represents —O— or —NH—;
$R^4$ represents H or an electron withdrawing group bound to an ortho or a para position of the -Y-L-X group;
A represents —C≡C-E where, E represents —COOH, —H, —CN, —COO-alkyl, or, an aryl group, a pyridinyl group, a pyridinium group, a 3H-indolyl group, or a 3H-indol-1-ium group, optionally substituted with a substituent, or an aryl group substituted with an electron withdrawing group; and
an aqueous solvent.

12. The composition according to claim 11, further comprising a surfactant.

13. A reagent for assaying an analyte in a sample, the reagent comprising a compound represented by formula I, or a salt thereof:

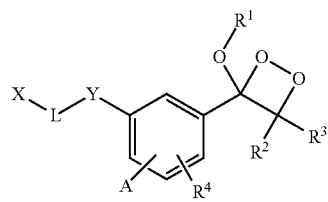

where,
$R^1$ represents a $C_{1-8}$ alkyl group,
each of $R^2$ and $R^3$ independently represents a $C_{3-18}$ alkyl group or a $C_{3-7}$ cycloalkyl group;
$R^1$ and $R^2$, $R^1$ and $R^3$, or $R^2$ and $R^3$, together with a carbon atom to which they are bound, may form an optionally substituted ring;
X represents a caging group;
L is absent or represents a linker represented by formula L1, L2, L3, or L4:

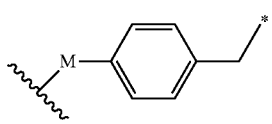

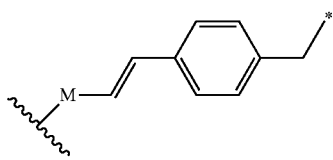

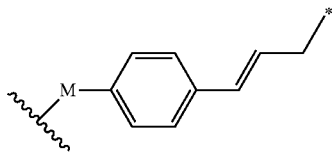

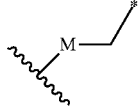

in each formula,
M is absent or represents —O— or —NH—,
a wavy line represents a linkage point to X,
an asterisk represents a linkage point to Y;
a benzene ring in formulae L1, L2, and L3 may be substituted with a substituent selected from the group consisting of halo group, alkyl group, cycloalkyl group, and alkoxy group;
Y is absent or represents —O— or —NH—;

R⁴ represents H or an electron withdrawing group bound to an ortho or a para position of the -Y-L-X group;

A represents —C≡C-E where, E represents —COOH, —H, —CN, —COO-alkyl, or, an aryl group, a pyridinyl group, a pyridinium group, a 3H-indolyl group, or a 3H-indol-1-ium group, optionally substituted with a substituent, or an aryl group substituted with an electron withdrawing group.

14. A reagent kit for assaying an analyte in a sample, the reagent kit comprising:

a first reagent comprising: a compound represented by formula I, or a salt thereof:

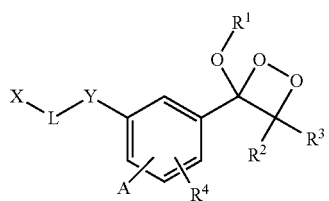

I where,

R¹ represents a $C_{1-8}$ alkyl group, each of R² and R³ independently represents a $C_{3-18}$ alkyl group or a $C_{3-7}$ cycloalkyl group;

R¹ and R², R¹ and R³, or R² and R³, together with a carbon atom to which they are bound, may form an optionally substituted ring;

X represents a caging group;

L is absent or represents a linker represented by formula L1, L2, L3, or L4:

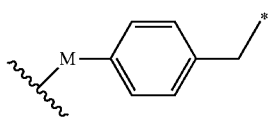

L1

-continued

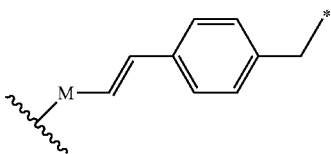

L2

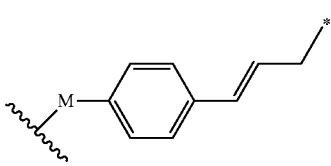

L3

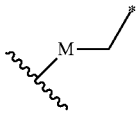

L4 in each formula,

M is absent or represents —O— or —NH—, a wavy line represents a linkage point to X, an asterisk represents a linkage point to Y;

a benzene ring in formulae L1, L2, and L3 may be substituted with a substituent selected from the group consisting of halo group, alkyl group, cycloalkyl group, and alkoxy group;

Y is absent or represents —O— or —NH—;

R⁴ represents H or an electron withdrawing group bound to an ortho or a para position of the -Y-L-X group;

A represents —C≡C-E where, E represents —COOH, —H, —CN, —COO-alkyl, or, an aryl group, a pyridinyl group, a pyridinium group, a 3H-indolyl group, or a 3H-indol-1-ium group, optionally substituted with a substituent, or an aryl group substituted with an electron withdrawing group; and a second reagent comprising a substance that releases the caging group.

* * * * *